(12) United States Patent
Belfield

(10) Patent No.: US 7,291,442 B1
(45) Date of Patent: Nov. 6, 2007

(54) PHOTOSENSITIVE POLYMERIC MATERIAL FOR WORM OPTICAL DATA STORAGE WITH TWO-PHOTON FLUORESCENT READOUT

(75) Inventor: Kevin D. Belfield, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 6 days.

(21) Appl. No.: 11/256,552

(22) Filed: Oct. 21, 2005

Related U.S. Application Data

(62) Division of application No. 10/306,960, filed on Nov. 27, 2002, now Pat. No. 7,001,708.

(60) Provisional application No. 60/339,283, filed on Dec. 11, 2001, provisional application No. 60/333,972, filed on Nov. 28, 2001.

(51) Int. Cl.
G03F 7/004 (2006.01)

(52) U.S. Cl. .................. 430/270.1; 430/905; 430/907; 430/910

(58) Field of Classification Search ............. 430/270.1, 430/905, 910, 907
See application file for complete search history.

(56) References Cited

U.S. PATENT DOCUMENTS

| | | | | |
|---|---|---|---|---|
| 4,458,345 | A | 7/1984 | Bjorklund et al. | 369/103 |
| 5,253,198 | A | 10/1993 | Birge et al. | 365/106 |
| 5,268,862 | A | 12/1993 | Rentzepis | 365/151 |
| 5,289,407 | A | 2/1994 | Strickler et al. | 365/106 |
| 5,912,257 | A | 6/1999 | Prasad et al. | 514/356 |
| 6,267,913 | B1 | 7/2001 | Marder et al. | 252/582 |
| 6,310,850 | B1 | 10/2001 | Sochava et al. | 369/103 |
| 2001/0018099 | A1 | 8/2001 | Gibbons et al. | 428/1.27 |
| 2001/0028620 | A1 | 10/2001 | Guerra | 369/112.16 |
| 2001/0030934 | A1 | 10/2001 | Lipson et al. | 369/275.4 |

OTHER PUBLICATIONS

P. Cheben, M. Calvo, A photopolymerizable glass with diffraction efficiency near 100% for holographic storage, Appl. Phys. Lett, Mar. 12, 2001, vol. 78, No. 11, pp. 1490-1492.
K. Belfield, C. Chinna, O. Najjar, S. Sriran and K. Schafer, Methodology for the Synthesis of New Multifunctional Polymers for Photorefractive Applications, in Field Responsive Polymers, ACS Symposium Series 726, American Chemical Society, pp. 250-263, no date avail.
K. Belfield, D. Hagan, Y. Liu, R. Negres, M. Fan, and F. Hernandez, Two-photon photochromism of a photorefractive organic material for holographic recording, Proc. SPIE—Int. Soc. Opt. Eng., 2000 (in press).
J. Kim, T. Chang, J. Kang, K. Park, D. Han and K. Ahn, Photoacid-Induced Fluorescence Quenching: A New Strategy for Fluorescent Imaging in Polymer Films, Angew. Chem. Int. Ed. 2000, 39, No. 10, pp. 1780-1782.

K. Belfield, K. Schafer, Y. Liu, J. Liu, X. Ren and E. Van Stryland, Multiphoton-absorbing organic materials for microfabrication, emerging optical applications and non-destructive three-dimensional imaging, J. Phys. Org. Chem., 2000, 13, pp. 837-849.
W. Denk, J. Strickler, W. Webb, Two-Photon Laser Scanning Fluorescence Microscopy, SCIENCE, vol. 248, pp. 73-76, no date avail.
R. Birge, B. Parson, Q. Song, J. Tallent, Protein-based Three-dimensional Memories and Associative Processors, in Molecular Electronics, Chapter 15, pp. 439-472, no date avail.
K. Belfield, K. Schafer, S. Andrasik, O. Yavuz, E. Van Stryland, D. Hagan and J. Hales, Three-dimensional two-photon imaging in polymeric materials, SPIE 2001 (submitted).
D. Parthenopoulos and P. Rentzepis, Three-Dimensional Optical Storage Memory, SCIENCE vol. 245, Aug. 25, 1989, pp. 843-845.
G. Pohlers and J. Scaiano, A Novel Photometric Method for the Determination of Photoacid Generation Efficiencies Using Benzothiazole and Xanthrene Dyes as Acid Sensors, Chem. Mater., vol. 9, No. 12, 1997, pp. 3222-3230.
K. Belfield, K. Schafer, W. Mourad and B. Reinhardt, Synthesis of New Two-Photon Absorbing Fluorene Derivatives via Cu-Mediated Ullmann Condensations, The Journal of Organic Chemistry, vol. 65, No. 15, Jul. 28, 2000, pp. 4475-4481.
K. Belfield, D. Hagan, E. Van Stryland, K. Schafer, and R. Negres, New Two-Photon Absorbing Fluorene Derivatives: Synthesis and Nonlinear Optical Characterization, Organic Letters, 1999, vol. I, No. 10, pp. 1575-1578.
K. Belfield and J. Wang, Modified Horner-Emmons Reaction of Polymeric Phosphonates: Versatile Synthesis of Pendant Stilbene-Containing Polymers, Journal of Polymer Science, Part A, Polymer Chemistry, 1995, vol. 33, pp. 1235-1242.
K. Belfield and K. Schafer, A New Photosensitive Polymeric Material for WORM Optical Data Storage Using Multichannel Two-Photon Fluorescence Readout, Chem. Mater. 2002, 14, pp. 3656-3662.

*Primary Examiner*—John S. Chu
(74) *Attorney, Agent, or Firm*—Brian S. Steinberger; Joyce P. Morlin; Law Offices of Brian S. Steinberger, P.A.

(57) ABSTRACT

Image formation via photoinduced fluorescence changes in a polymeric medium with two-photon fluorescence readout of a multi-layer structure. Fluorophore-containing polymers, possessing one or more basic functional groups, underwent protonation in the presence of a photoinduced acid generator upon exposure to a broad-band UV light source or fast-pulsed red to near-IR laser irradiation. Solution studies demonstrated formation of monoprotonated and diprotonated species upon irradiation, each resulting in distinctly different absorption and fluorescence properties. The fluorescence of the original, neutral, fluorophore was reduced upon monoprotonation, leading to a concomitant increase in fluorescence at longer wavelengths due to the monoprotonated form, the basis for multichannel data readout. Experiments in polymer films demonstrate the changes in fluorescence properties of the photosensitive polymer compositions and polymers can be employed for a high storage density, write-once read-many (WORM) data storage medium with two-photon fluorescence readout. Two-channel, two-photon fluorescence imaging provided both "positive" and "negative" image readout capability.

2 Claims, 12 Drawing Sheets

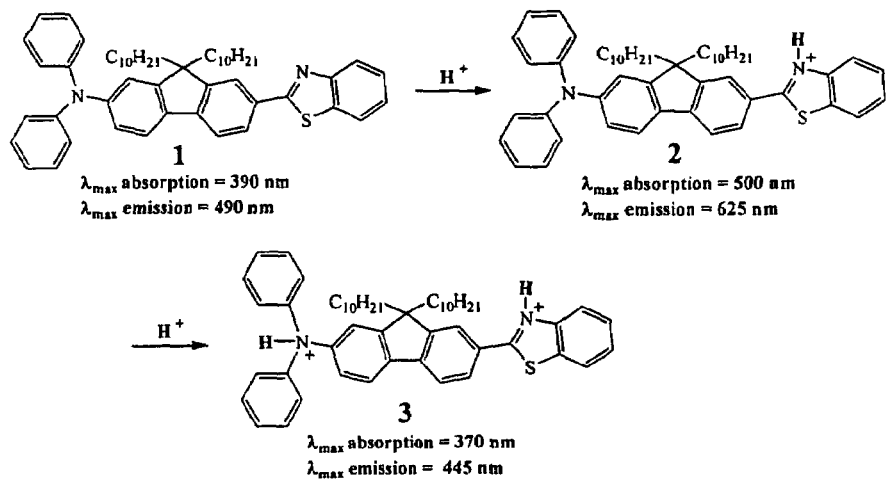
Figure 1 shows the reaction of fluorene dye 1 with acid resulting in the formation of monoprotonated 2 and diprotonated 3 products.
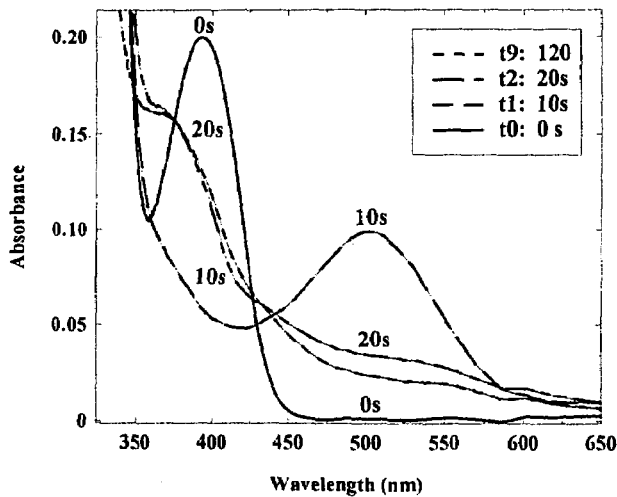
Figure 2 is a graphical representation of the time-dependent UV-visible absorption spectra of the photolysis of fluorene 1 and photoacid generator in $CH_2Cl_2$ at photolysis times from 0 to 120 sec.

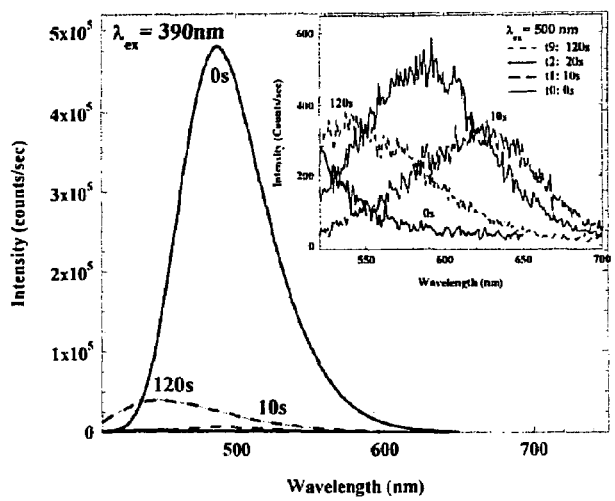

Figure 3 is a graphical representation of the time-dependent fluorescence emission spectra for the photolysis of fluorene 1 and photoacid generator in $CH_2Cl_2$ at photolysis times from 0 to 120 sec (excitation at 390 nm) with an inset that shows fluorescence at longer wavelength with excitation at 500 nm.

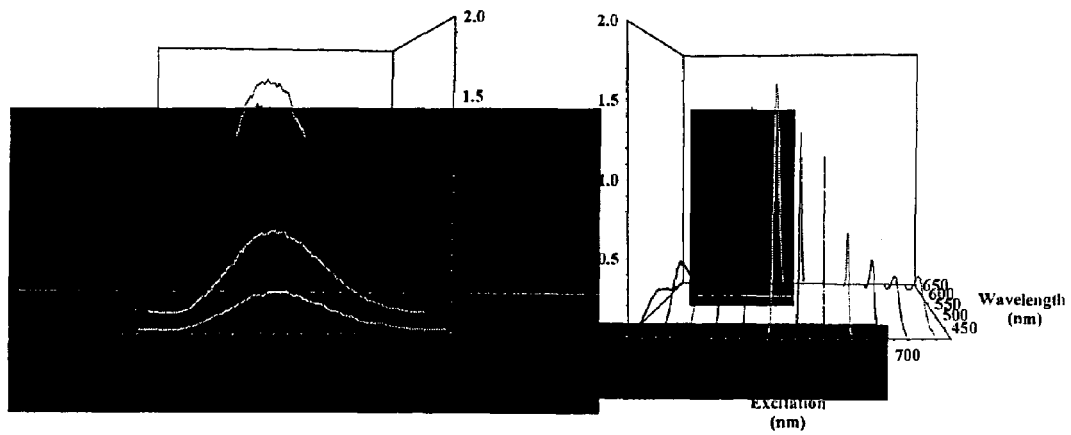

Figure 4 Two-photon upconverted fluorescence emission spectra of 1 at several fs pulsed pump wavelengths ($2.5 \times 10^{-4}$ M, ACN).

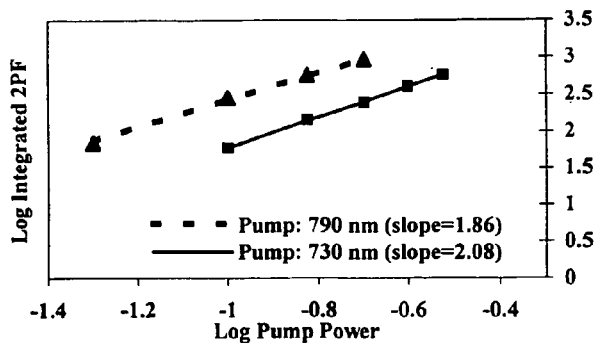
Figure 5. Plot of the total integrated fluorescence intensity of 1 as a function of pump power at two fs pump wavelengths.
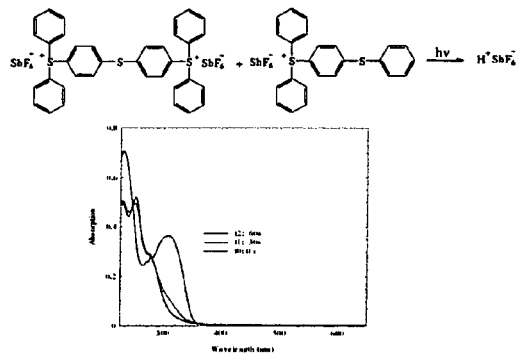
Figure 6. Photoacid generation and time-dependent absorption spectra of PAG.

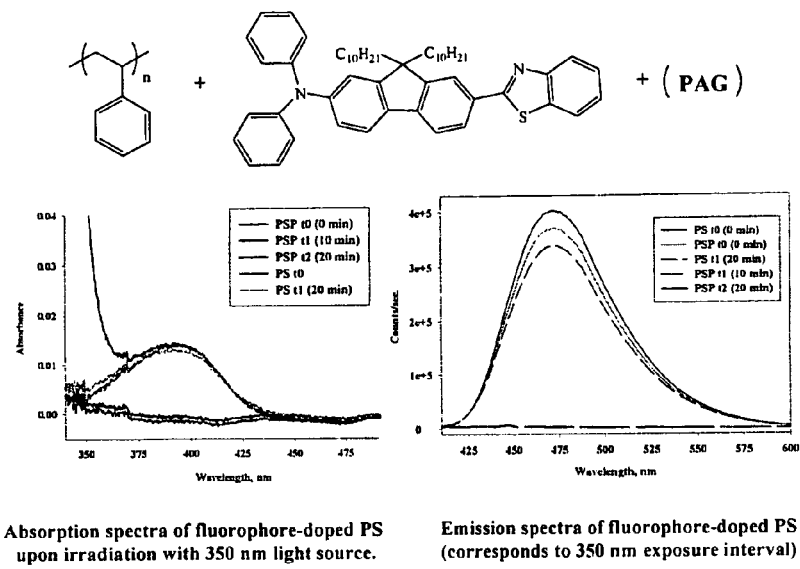
Figure 7. Time-dependent absorption and fluorescence spectra of PAG and dye containing polymer in solution.
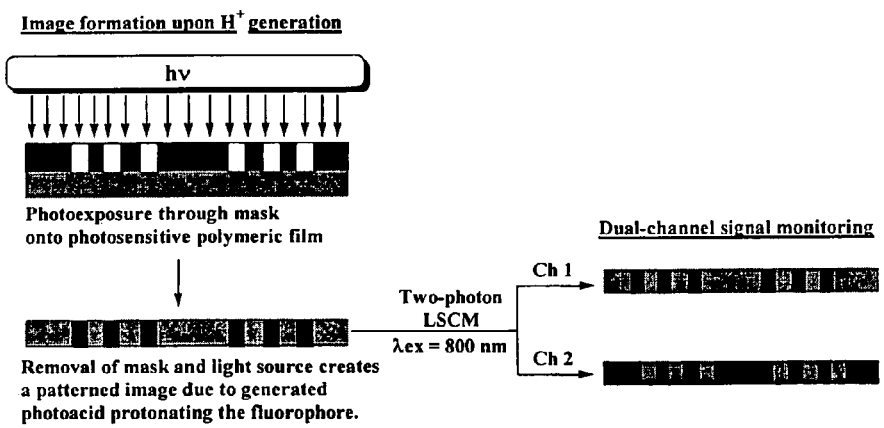
Figure 8. Diagram of image formation within a photosensitive polymeric film containing PAG, and acid-sensitive fluorophore, allowing two-photon induced, dual-channel fluorescence imaging.

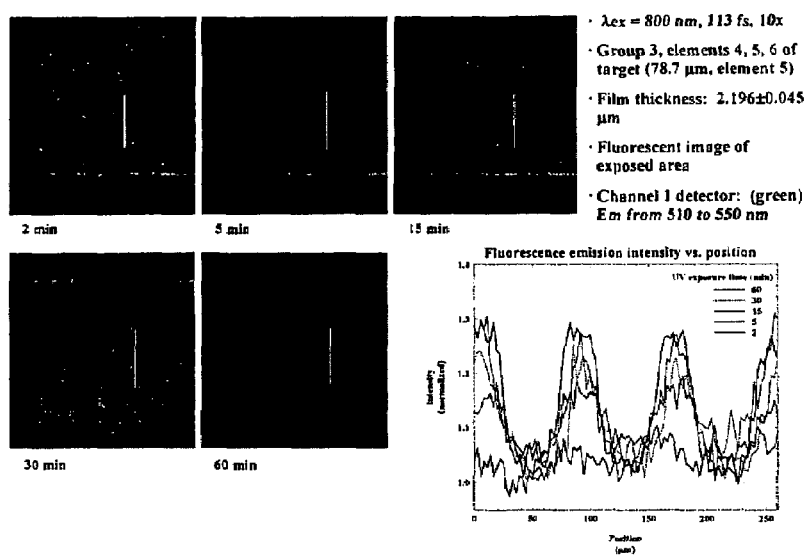

Figure 9. Two-photon fluorescent images of photosensitive films developed (via 350 nm broadband exposure, 4.4 mW/cm$^2$) using an Air Force resolution target mask. Image recorded by channel 1 at various exposure times. Data readout as a function of exposure time determined from fluorescence intensity by scanning an xy line across one set of three-member elements (yellow line across set 5).

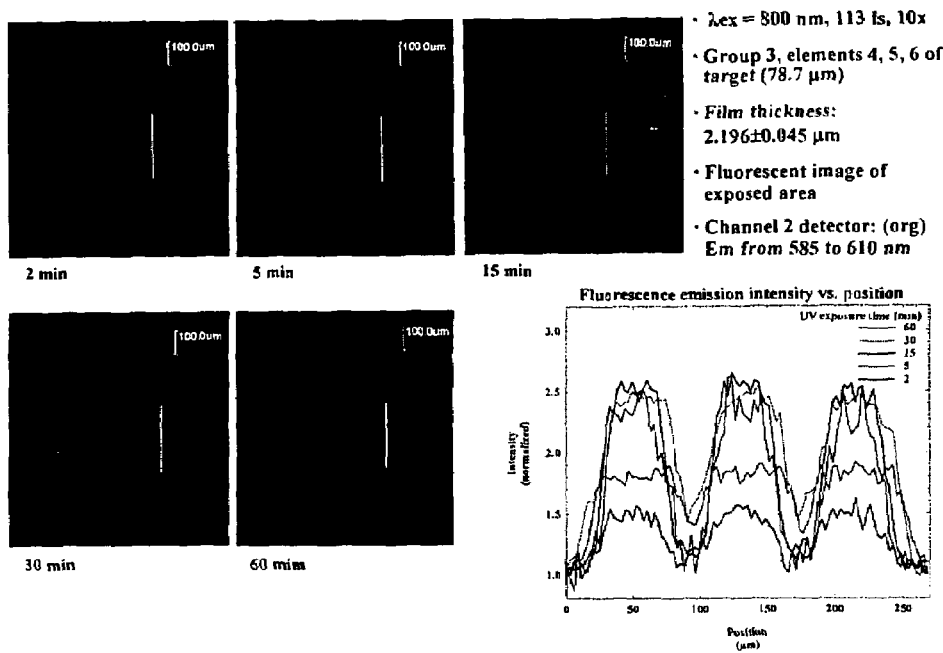

Figure 10. Two-photon fluorescent images of photosensitive films developed (via 350 nm broadband exposure, 4.4 mW/cm$^2$) using an Air Force resolution target mask. Image recorded by channel 2 at various exposure times. Data readout as a function of exposure time determined from fluorescence intensity by scanning an xy line across one set of three-member elements (yellow line across set 5).

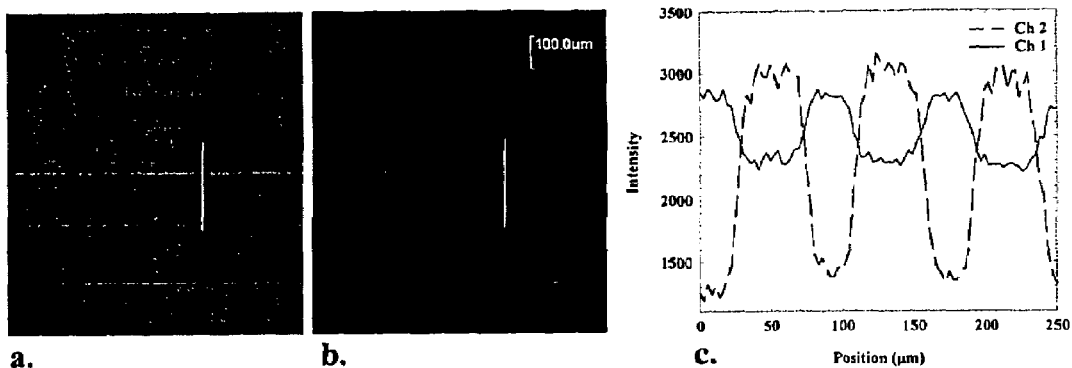

Figure 11. Two-photon fluorescent images of photosensitive films developed (via 350 nm broadband exposure, 4.4 mW/cm$^2$) using an Air Force resolution target mask. (a) Image recorded by channel 1, (b) image recorded by channel 2, and (c) fluorescence intensity by scanning an xy line across one set of three-member elements (yellow line across set 5) clearly shows the reverse parity of the signals.

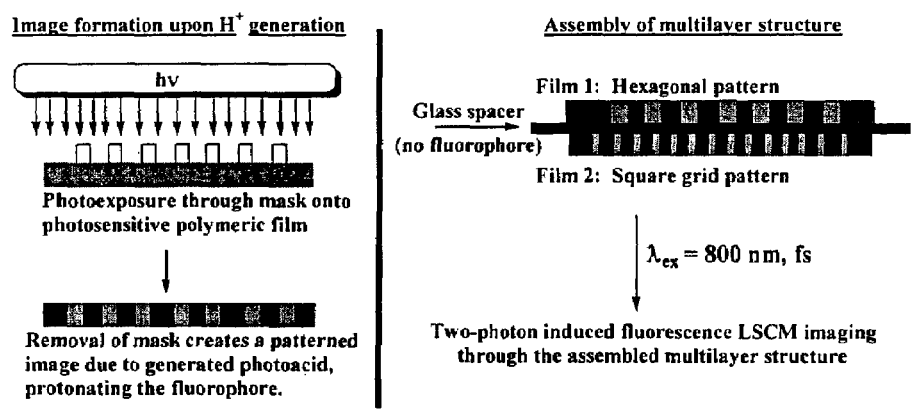

Figure 12. Image formation (upon photoacid generation) within photosensitive polymer films for assembly of multi-layered structures. Two-photon fluorescence LSCM imaging using fs pulsed near-IR pump allows for 3-D volumetric imaging of the layered structure.

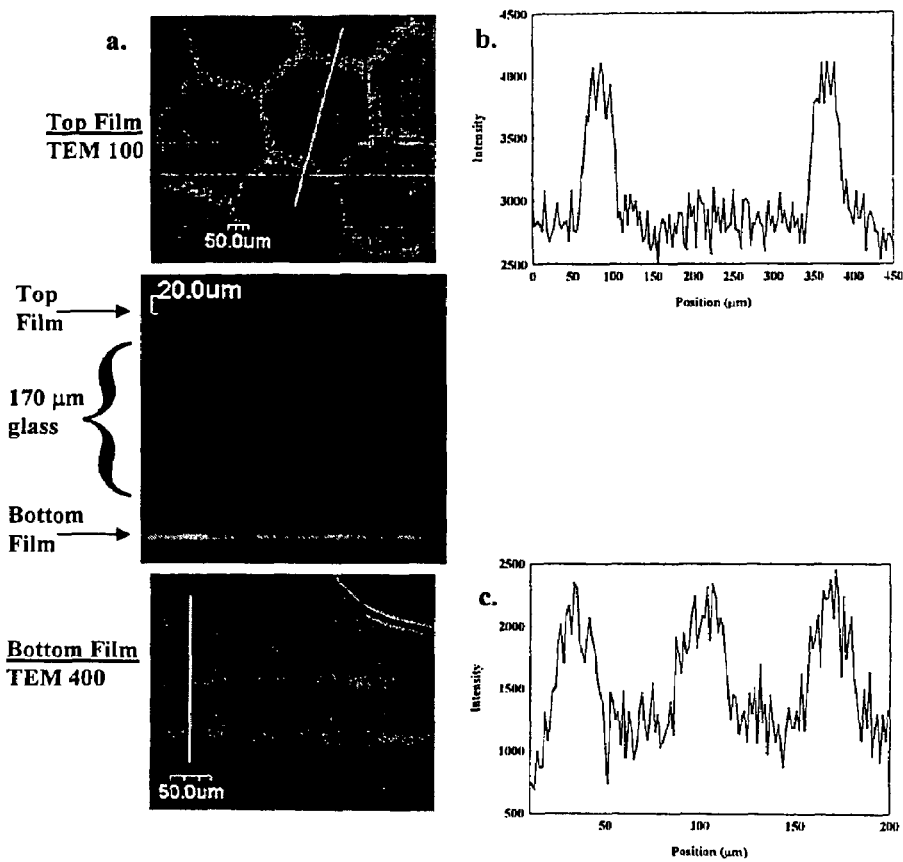

Figure 13. (a) Two-photon fluorescent images of multi-layered films developed via 350 nm: broadband irradiation (6.0 mW/cm$^2$) by exposure through TEM hexagonal and square grid masks. Fluorescence intensity plots for a line scan across a region (as defined by the yellow line across the image area) provides (b) image readout in one layer, and (c) changing the depth (z position) for image (signal) readout in the lower layer within a multi-layered system.

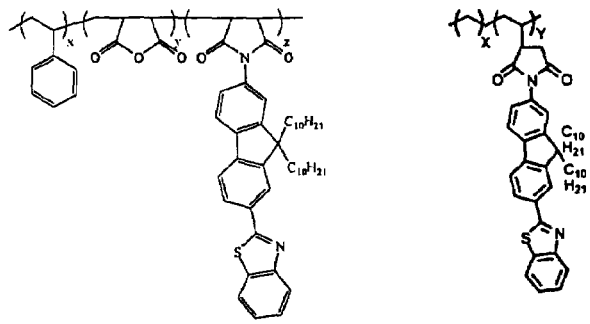

Figure 14. Structure of photosensitive polymers.

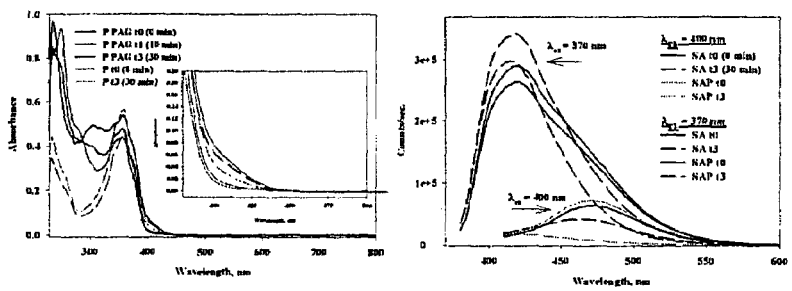

Figure 15. Absorption and fluorescence emission spectra of polystyrene based photosensitive polymers with and without PAG.

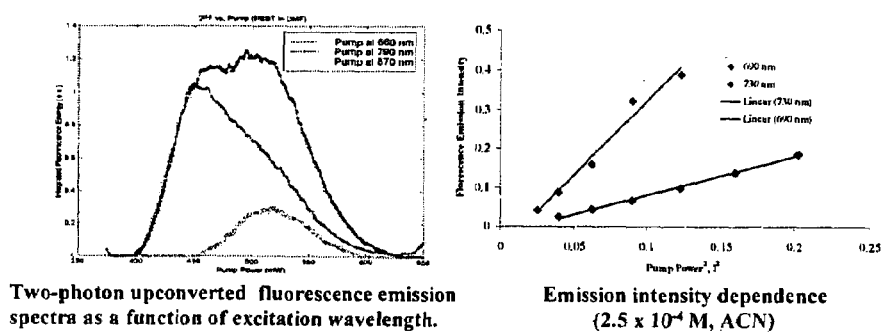

Two-photon upconverted fluorescence emission spectra as a function of excitation wavelength.

Emission intensity dependence
(2.5 x 10⁻⁴ M, ACN)

Figure 16. Two-photon upconverted fluorescence emission spectra of polystyrene based photosensitive polymers, and demonstration of two-photon absorption via quadratic intensity dependence.

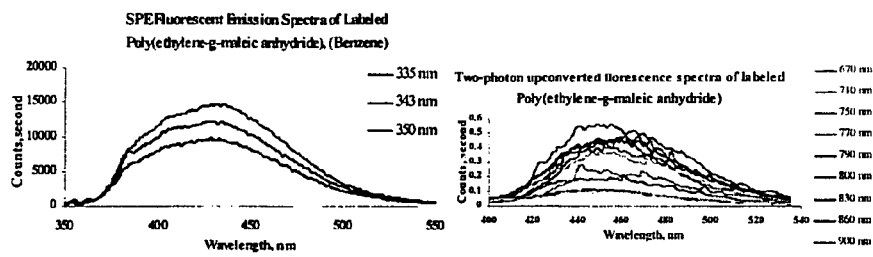

Figure 17. Single-photon and two-photon upconverted fluorescence emission spectra of polyethylene based photosensitive polymers.

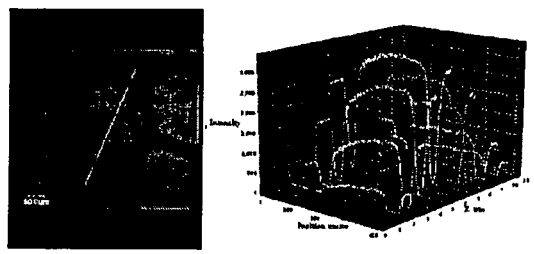

Figure 18. Two-photon fluorescence image of the exposed photosensitive polymer without PAG is shown (left), along with the fluorescence intensity profile through the bulk (xyz scan) of the film.

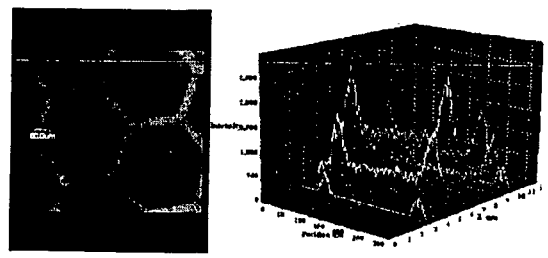

Figure 19. Two-photon fluorescence image of the exposed photosensitive polymer with PAG is shown (left), along with the fluorescence intensity profile through the bulk (xyz scan) of the film.

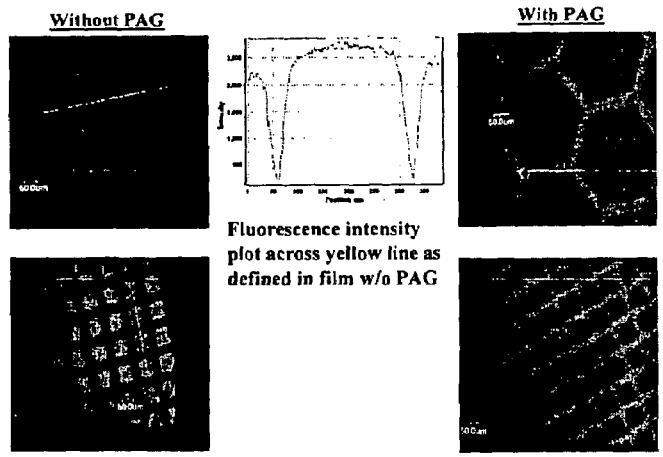

Figure 20. Two-photon fluorescence image of the exposed photosensitive polymer without and with PAG are shown (left and right, respectively), along with the fluorescence intensity data readout.

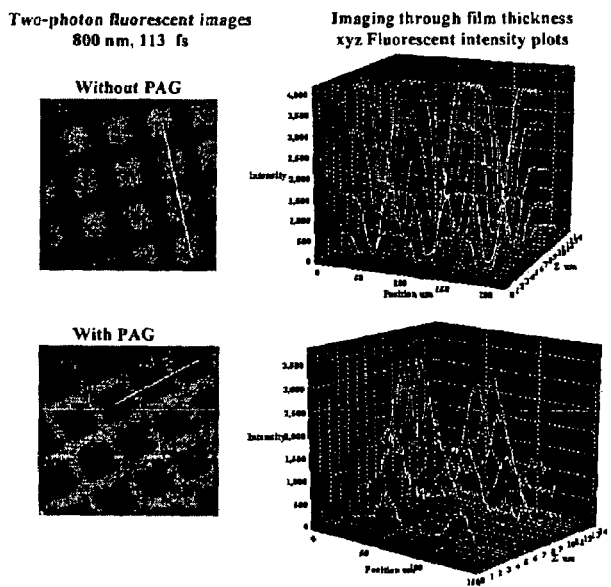

Figure 21. Two-photon fluorescence image of the exposed photosensitive polymer without and with PAG are shown (top and bottom, respectively), along with the 3-D fluorescence intensity data readout.

Figure 22. Demonstration of two-photon writing and readout in photosensitive polymer.
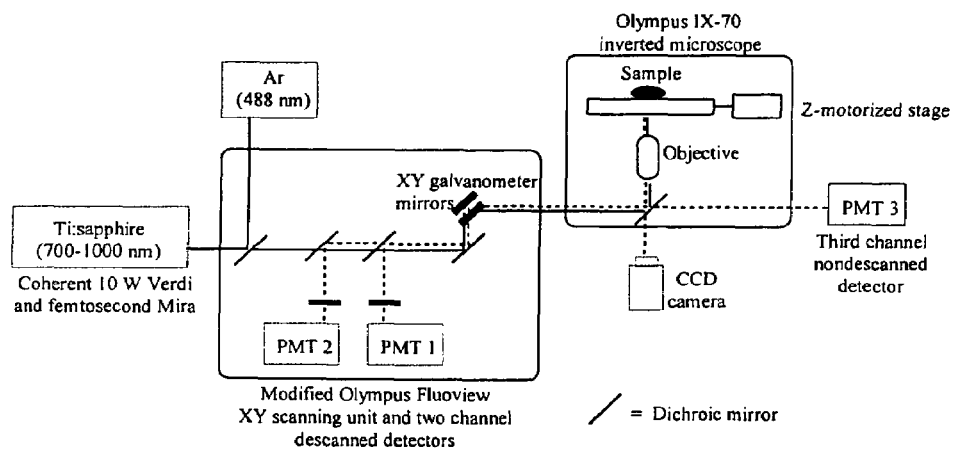
Figure 23. Schematic diagram of two-photon writing and recording system.

PHOTOSENSITIVE POLYMERIC MATERIAL FOR WORM OPTICAL DATA STORAGE WITH TWO-PHOTON FLUORESCENT READOUT

FIELD OF THE INVENTION

This is a Divisional of application Ser. No. 10/306,960 filed Nov. 27, 2002 now U.S. Pat. No. 7,001,708 which claims priority of U.S. Provisional Application 60/339,283 filed Dec. 11, 2001 and U.S. Provisional Application 60/333,972 filed Nov. 28, 2001.

BACKGROUND OF THE INVENTION

Over the past 50 years, the field of organic photochemistry has produced a wealth of information, from reaction mechanisms to useful methodology for synthetic transformations. Many technological innovations have been realized during this time due to the exploits of this knowledge, including photoresists and lithography for the production of integrated circuits, photocharge generation for xerography, multidimensional fluorescence imaging, photodynamic therapy for cancer treatment, photoinitiated polymerization, and UV protection of plastics and humans through the development of UV absorbing compounds and sunscreens, to name a few.

The scientific basis of many of these processes continues to be utilized today, particularly in the development of organic three-dimensional optical data storage media and processes.

With the ever-pressing demand for higher storage densities, researchers are pursuing a number of strategies to develop three-dimensional capabilities for optical data storage in organic-based systems. Among the various strategies reported are holographic data storage using photopolymerizable media (Cheben, P. and Calvo, M. Appl. Phys. Lett. 2001, 78, 1490; U.S. Pat. No. 5,289,407 and U.S. Pat. No. 6,310,850), photorefractive polymers (Belfield et al. Field Responsive Polymers, ACS Symposium Series 726, ACS, 1999, Chapter 17), and two-photon induced photochromism (Belfield et al. Organic Photorefractives, Photoreceptors, and Nanocomposites, Proc. SPIE Vol. 4104, 2000, 15-22; U.S. Pat. No. 5,268,862). It is known that fluorescent properties of certain fluorophores may be changed (quenched) upon protonation by photogeneration of acid (Kim et al. Angew. Chem. Int. Ed. 2000, 39, 1780). Belfield et al. J. Phys. Org. Chem. 2000, 13, 837 has reported two-photon induced photoacid generation using onium salts and short pulsed near-IR lasers in the presence of a polymerizable medium, resulting in two-photon photoinitiated cationic polymerization. The inherent three-dimensional features associated with two-photon absorption provides an intriguing basis upon which to combine spatially-resolved, two-photon induced photoacid generation and fluorescence quenching with two-photon fluorescence imaging.

The quadratic, or nonlinear, dependence of two-photon absorption on the intensity of the incident light has substantial implications ($dw/dt \propto I^2$). For example, in a medium containing one-photon absorbing chromophores significant absorption occurs all alone the path of a focused beam of suitable wavelength light. This can lead to out-of focus excitation. In a two-photon process, negligible absorption occurs except in the immediate vicinity of the focal volume of a light beam of appropriate energy. This allows spatial resolution about the beam axis as well as radially, which circumvents out-of-focus absorption and is the principle reason for two-photon fluorescence imaging (Denk et al. Science 1989, 248, 73). Particular molecules can undergo upconverted fluorescence through nonresonant two-photon absorption using near-IR radiation, resulting in an energy emission greater than that of the individual photons involved (upconversion). The use of a longer wavelength excitation source for fluorescence emission affords advantages not feasible using conventional UV or visible fluoresence techniques e.g., deeper penetration of the excitation beam and reduction of photobleaching, and is particularly well-suited for fluorescence detection in multilayer coatings.

U.S. Pat. No. 5,268,862 reported two-photon induced photochromism of spiropyran derivatives at 1064 nm. Analogous to single-photon absorption facilitated isomerizion, the spiropyran underwent ring-opening isomerizion to the zwitterionic colored merocyanine isomer. The merocyanine isomer underwent two-photon absorption at 1064 nm, resulting in upconverted fluorescence. However, spiropyrans are known to undergo photobleaching and photodegradation upon prolonged exposure with blurring effects observed outside the irradiated volume, and hence are not suitable for long-term use. U.S. Pat. No. 5,253,198 disclosed a bacteriorhodopsin-based holographic recording media and process, using two-photon excitation. High data storage and photostabilities were reported for this rather complex system, however it requires near-zero gravity conditions for processing to ensure homogeneous distribution of the bacteriorhodopsin, an electrochemical system to measure the electrical response vs. a purely optical response, and careful handling of the biological material (the protein). Though the read time claimed of 100 ns is impressive, as are read data rates of up to 10 Mbit/sec, the complexity of the system seriously undermines any practical potential applications of the system.

Thus, in addition to high data storage volume and fast readout, there is a need for data storage materials that are stable, highly responsive, exhibit high sensitivity and fidelity, and are less complex. In addition, the data storage and readout processes must also be more straight forward (less complex) and reliable. As mentioned above, the previously developed systems fall short in these regards.

SUMMARY OF THE INVENTION

The invention described herein relates to high density random access data storage, and is particularly more directed to materials for an optical memory system in which near-IR laser light is employed to write and read data via two-photon processes within an irradiated area which can be controlled in three-dimensions.

It is an objective of the invention to develop a high density optical data storage system in which optical properties of the medium can be modulated and read in three-dimensions via two-photon processes.

Another object of the invention is to develop optical materials to enable two-photon induced photochemical changes suitable for two-photon fluorescent readout.

Another object of the invention is to harness the high photosensitivity of the photosensitive polymers to create a high density optical data storage system with multichannel readout capability to further increase data storage and readout versatility.

Another object of the invention is to incorporate structural constructs of the fluorophores into polymers, creating photoresponsive polymers with extraordinarily high photosensitivity.

A preferred embodiment of the invention is the use of a photosensitive polymeric material for WORM optical data storage with two-photon fluorescent readout comprising fluorophore compounds of the present invention admixed with a polymer. Further preferred embodiments of the invention include (1) a WORM optical data storage device suitable for imposing information on it comprising a disk structure suitable for structurally supporting a polymer film containing about 0.01 to about 5.0 wt % of the fluorophore and about 0.5 to about 20.0 wt % of photoaid generator (PAG), relative to the polymer and said polymer film supported by said disk structure and (2) said optical data storage device in a readable state wherein said polymer film has been irradiated to decrease the fluorescence concentration of the neutral fluorophore and increase the fluorescence of monoprotonated fluorophore whereby the resulting stored optical information can be recovered via multichannel readout.

Several of these fluorophores and polymers undergo substantial changes in the absorption and fluorescence spectral properties in the presence of strong acid, i.e., they undergo protonation, affording changes in their polarizability, absorption and emission maxima and fluorescence quantum yields.

Further objects and advantages of this invention will be apparent from the following detailed descriptions of presently preferred embodiments which are illustrated schematically in the accompanying drawings.

BRIEF DESCRIPTION OF THE FIGURES

FIG. 1 shows the reaction of fluorene dye 1 with acid resulting in the formation of monoprotonated 2 and diprotonated 3 products.

FIG. 2 is a graphical representation of the time-dependent UV-visible absorption spectra of the photolysis of fluorene 1 and photoacid generator in $CH_2Cl_2$ at photolysis times from 0 to 120 sec.

FIG. 3 is a graphical representation of the time-dependant fluorescence emission spectra for the photolysis of fluorene 1 and photoacid generator in $CH_2Cl_2$ at photolysis times from 0 to 120 sec (excitation at 390 nm) with an inset that shows fluorescence at longer wavelength with excitation at 500 nm.

FIG. 4 shows two-photon upconverted fluorescence emission spectra of fluorine 1 at several fs pulsed pump wavelengths ($2.5 \times 10^{-4}$ M, ACN).

FIG. 5 shows the plot of the total integrated fluorescence intensity of fluorine 1 as a function of pump power at two fs pump wavelengths.

FIG. 6 shows photoacid generation and time-dependent absorption spectra of PAG.

FIG. 7 shows time-dependent absorption and fluorescence spectra of PAG and dye containing polymer in solution.

FIG. 8 displays a diagram of image formation within a photosensitive polymeric film containing PAG, and acid-sensitive fluorophore, allowing two-photon induced, dual-channel fluorescence imaging.

FIG. 9 shows two-photon fluorescent images of photosensitive films developed (via 350 nm broadband exposure, 4.4 $mW/cm^2$) using an Air Force resolution target mask. Image recorded by channel 1 at various exposure times. Data readout as a function of exposure time determined from fluorescence intensity by scanning an xy line across one set of three-member elements (yellows line across set 5).

FIG. 10 shows two-photon fluorescent images of photosensitive films developed (via 350 nm broadband exposure, 4.4 $mW/cm^2$) using an Air Force resolution target mask. Image recorded by channel 2 at various exposure times. Data readout as a function of exposure time determined from fluorescence intensity by scanning an xy line across one set of three-member elements (yellow line across set 5).

FIG. 11 shows two-photon fluorescent images of photosensitive films developed (via 350 nm broadband exposure, 4.4 $mW/cm^2$) using an Air Force resolution target mask. (a) Image recorded by channel 1, (b) image recorded by channel 2, and (c) fluorescence intensity by scanning an xy line across one set of three-member elements (yellow line across set 5) clearly shows the reverse parity of the signals.

FIG. 12 shows image formation (upon photoacid generation) within photosensitive polymer films for assembly of multi-layered structures. Two-photon fluorescence LSCM imaging using fs pulsed near-IR pump allows for 3-D volumetric imaging of the layered structure.

FIG. 13 shows (a) two-photon fluorescent images of multi-layered films developed via 350 mm: broadband irradiation (6.0 $mW/cm^2$) by exposure through TEM hexagonal and square grid masks. Fluorescence intensity plots for a line scan across a region (as defined by the yellow line across the image area) provides (b) image readout in one layer, and (c) changing the depth (z position) for image (signal) readout in the lower layer within a multi-layered system.

FIG. 14 gives the structure of two photosensitive polymers.

FIG. 15 shows absorption and fluorescence emission spectra of polystyrene based photosensitive polymers with and without PAG.

FIG. 16 shows two-photon upconverted fluorescence emission spectra of polystyrene based photosensitive polymers, and demonstration of two-photon absorption via quadratic intensity dependence.

FIG. 17 shows single-photon and two-photon upconverted fluorescence emission spectra of polyethylene based photosensitive polymers.

FIG. 18 shows two-photon fluorescence image of the exposed photosensitive polymer without PAG (left), alone with the fluorescence intensity profile through the bulk (xyz scan) of the film.

FIG. 19 shows two-photon fluorescence image of the exposed photosensitive polymer with PAG (left), along with the fluorescence intensity profile through the bulk (xyz scan) of the film.

FIG. 20 shows two-photon fluorescence image of the exposed photosensitive polymer without and with PAG (left and right, respectively), along with the fluorescence intensity data readout.

FIG. 21 shows two-photon fluorescence image of the exposed photosensitive polymer without and with PAG (top and bottom, respectively), along with the 3-D fluorescence intensity data readout.

FIG. 22 demonstrates two-photon writing and readout in photosensitive polymer.

FIG. 23 shows a schematic diagram of two-photon writing and recording system.

DESCRIPTION OF THE PREFERRED EMBODIMENTS

Thus, in a first embodiment, the present invention provides a photosensitive composition comprising:

(a) a fluorophore compound of Formula I:

$$X-U-Y-V-Z \quad \text{I}$$

wherein X is selected from the group:

—NH$_2$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), 2-thiazolyl substituted with 0-2 R$^2$; 2-oxazolyl substituted with 0-2 R$^2$; 2-benzothiazolyl substituted with 0-4 R$^2$;

2-benzoxazolyl substituted with 0-4 R$^2$; and 2- or 4-pyridyl substituted with 0-4 R$^2$, and N-carbazolyl substituted with 0-4 R$^2$;

Y is substituted with 0-5 R$^1$ and is selected from the group:

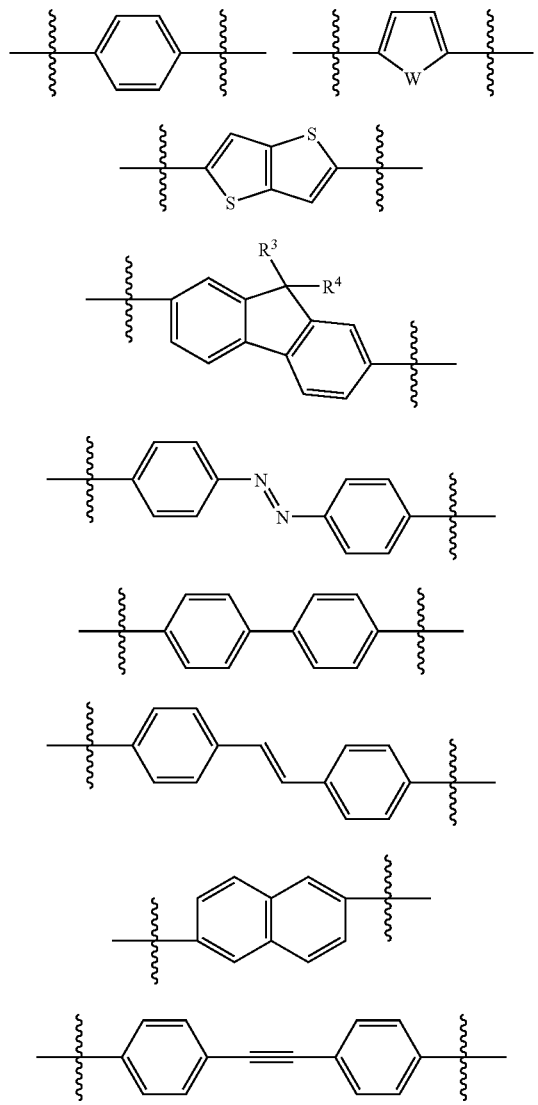

W is O, S, NH or N(C$_1$-C$_6$ alkyl);

Z is H, X, CN, —N=C=S, NO$_2$, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —P(=O)(OH)$_2$, —P(=O)(OH)(O—C$_1$-C$_6$ alkyl), —P(=O)(O—C$_1$-C$_6$ alkyl)$_2$, —N-succinimidyl, C$_1$-C$_{20}$ alkyl substituted with 0-5 R$^1$, C$_1$-C$_{20}$ alkenyl substituted with 0-5 R$^1$, C$_1$-C$_{20}$ alkynyl substituted with 0-5 R$^1$, C$_6$-C$_{14}$ aryl substituted with 0-5 R$^1$, or 5-14 membered heterocycle substituted with 0-5 R$^1$;

U and V, at each occurrence, are independently a bond, —CH=CH—, —CH=CH-phenylene-, or -phenylene-CH=CH—;

R$^1$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N=C=S, —NH(C=S)—O(C$_1$-C$_6$ alkyl), —NH(C=S)—NH(C$_1$-C$_6$ alkyl), or —NH(C=S)—N(C$_1$-C$_6$ alkyl)$_2$;

R$^2$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N=C=S, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —CO$_2$H, or —CO$_2$(C$_1$-C$_6$ alkyl); and R$^3$ and R$^4$, at each occurrence, are independently C$_1$-C$_{16}$ alkyl, C$_1$-C$_{10}$ haloalkyl, —(CH$_2$)$_{1-9}$CO$_2$H, —(CH$_2$)$_{1-9}$CO$_2$(C$_1$-C$_6$ alkyl), —(CH$_2$CH$_2$O)$_{1-6}$H, or —(CH$_2$CH$_2$O)$_{1-6}$(C$_1$-C$_6$ alkyl);

(b) a photoacid generator; and (c) a polymer binder.

In another embodiment, the present invention provides a photosensitive composition comprising:

(a) a fluorophore compound of Formula I:

X—U—Y—V—Z          I wherein X is selected from the group:

—NH$_2$, —NH(phenyl), —N(phenyl)$_2$, 2-thiazolyl substituted with 0-2 R$^2$; 2-oxazolyl substituted with 0-2 R$^2$; 2-benzothiazolyl substituted with 0-4 R$^2$; 2-benzoxazolyl substituted with 0-4 R$^2$; 2- or 4-pyridyl substituted with 0-4 R$^2$, and N-carbazolyl substituted with 0-4 R$^2$;

Y is substituted with 0-2 R$^1$ and is selected from the group:

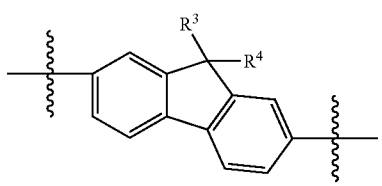

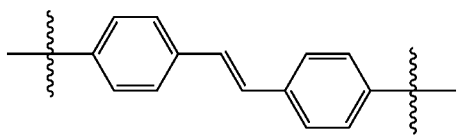

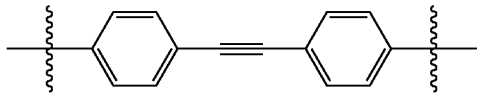

Z is H, X, CN, —N=C=S, NO$_2$, —NH(C=S)—O(C$_1$-C$_6$ alkyl), —NH(C=S)—NH(C$_1$-C$_6$ alkyl), —NH(C=S)—N(C$_1$-C$_6$ alkyl)$_2$, —P(=O)(OH)$_2$, —P(=O)(OH)(O—C$_1$-C$_6$ alkyl), —P(=O)(O—C$_1$-C$_6$ alkyl)$_2$, —N-succinimidyl, C$_1$-C$_{10}$ alkyl substituted with 0-5

$R^1$, $C_1$-$C_{10}$ alkenyl substituted with 0-5 $R^1$, $C_1$-$C_{10}$ alkynyl substituted with 0-5 $R^1$, phenyl substituted with 0-5 $R^1$, naphthyl substituted with 0-5 $R^1$, or 5-12 membered heterocycle substituted with 0-5 $R^1$; said heterocycle is selected from the group: pyridyl, pyrimidinyl, furanyl, thiazolyl, thienyl, pyrrolyl, imidazolyl, benzofuranyl, benzothiophenyl, benzoxazolyl, benzothiazolyl, indolyl, indolenyl, isoxazolinyl, quinolinyl, isoquinolinyl, benzimidazolyl, piperidinyl, pyrroiidinyl, triazinyl, chromenyl, xanthenyl, isothiazolyl, isoxazolyl, oxazolyl, isoindolyl, carbazolyl, phenanthridinyl, acridinyl, perimidinyl, phenanthrolinyl, morpholinyl, 1,4-benzoxazinyl;

U and V, at each occurrence, are independently a bond, —CH═CH—, —CH═CH-phenylene-, or -phenylene-CH═CH—;

$R^1$ is independently hydroxy, F, Cl, Br, I, $C_1$-$C_6$ alkoxy, $C_1$-$C_{10}$ alkyl, or $C_1$-$C_4$ haloalkyl;

$R^2$ is independently amino, hydroxy, F, Cl, Br, I, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —$CO_2$H, or —$CO_2$($C_1$-$C_6$ alkyl); and $R^3$ and $R^4$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl), —$(CH_2CH_2O)_{1-6}H$, or —$(CH_2CH_2O)_{1-6}(C_1$-$C_6$ alkyl);

(b) a photoacid generator; and,
(c) a polymer binder.

In another embodiment, the present invention provides a photosensitive composition comprising:

(a) a fluorophore compound of Formula I:

X—U—Y—V—Z    I wherein Y is

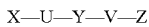

and substituted with 0-2 $R^1$;

(b) a photoacid generator; and
(c) a polymer binder.

In another embodiment, the present invention provides a photosensitive (polymer) composition, wherein the photoacid generator is selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate, dibutylnaphthylsulfonium triflate and mixtures thereof.

In another embodiment, the present invention provides a photosensitive composition, wherein the polymer binder is selected from the group: polystryene and its derivatives, polyacrylates, polymethacrylates, polycarbonates, polyurethanes, polysiloxanes, nylons, and polyesters.

In another embodiment, the present invention provides a photosensitive polymer composition comprising:

(a) a fluorophore-containing polymer comprising a unit selected from:

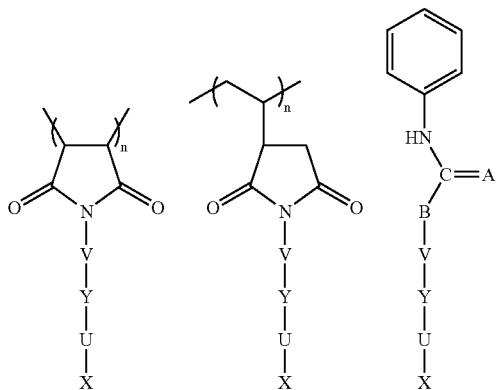

wherein X is selected from the group:

—$NH_2$, —NH($C_1$-$C_6$ alkyl), —N($C_1$-$C_6$ alkyl)$_2$, —NH(aryl), —N(aryl)$_2$, —NHCO($C_1$-$C_4$ alkyl), 2-thiazolyl substituted with 0-2 $R^2$; 2-oxazolyl substituted with 0-2 $R^2$; 2-benzothiazolyl substituted with 0-4 $R^2$;

2-benzoxazolyl substituted with 0-4 $R^2$; and 2- or 4-pyridyl substituted with 0-4 $R^2$, and N-carbazolyl substituted with 0-4 $R^2$;

Y is substituted with 0-5 $R^1$ and is selected from the group:

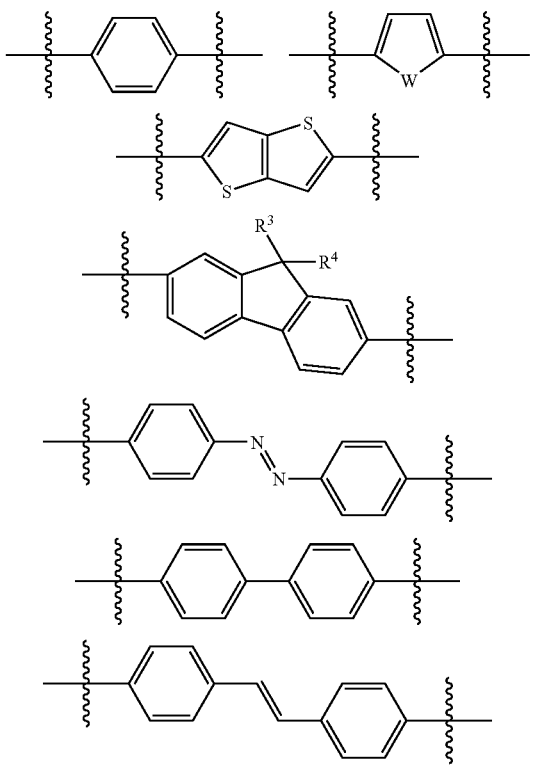

-continued

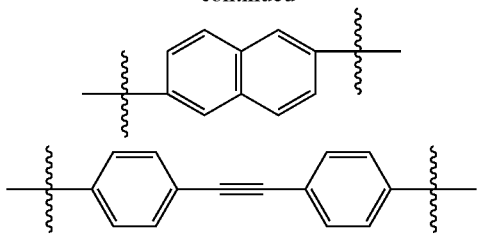

W is O, S, NH or N($C_1$-$C_6$ alkyl);

U and V, at each occurrence, are independently a bond, —CH=CH—, —CH=CH-phenylene-, or -phenylene-CH=CH—;

n is 1-50;

A is O or S;

B is O or NH;

$R^1$ is independently amino, hydroxy, halogen, $C_1$-$C_6$ alkoxyl, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH ($C_1$-$C_6$ alkyl), or —NH(C=S)—N($C_1$-$C_6$ alkyl)$_2$;

$R^2$ is amino, hydroxy, halogen, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO ($C_1$-$C_4$ alkyl), —N=C=S, —NH(C=S)—O($C_1$-$C_6$ alkyl), —NH(C=S)—NH($C_1$-$C_6$ alkyl), —NH (C=S)—N($C_1$-$C_6$ alkyl)$_2$, —$CO_2$H, or —$CO_2$($C_1$-$C_6$ alkyl); and $R^3$ and $R^4$, at each occurrence, are independently $C_1$-$C_{16}$ alkyl, $C_1$-$C_{10}$ haloalkyl, —($CH_2$)$_{1-9}$$CO_2$H, —($CH_2$)$_{1-9}$$CO_2$($C_1$-$C_6$ alkyl), —($CH_2CH_2$O)$_{1-6}$H, or —($CH_2CH_2$O)$_{1-6}$($C_1$-$C_6$ alkyl);

and, optionally, (b) a photoacid generator.

In another embodiment, the present invention provides a photosensitive polymer composition, comprising:

(a) a fluorophore-containing polymer comprising a unit selected from:

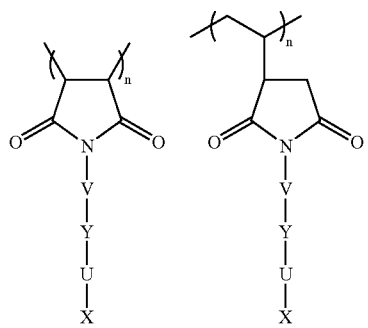

wherein X is selected from the group:

—$NH_2$, —NH(phenyl), —N(phenyl)$_2$, 2-thiazolyl substituted with 0-2 $R^2$; 2-oxazolyl substituted with 0-2 $R^2$; 2-benzothiazolyl substituted with 0-4 $R^2$; 2-benzoxazolyl substituted with 0-4 $R^2$; 2- or 4-pyridyl substituted with 0-4 $R^2$, and N-carbazolyl substituted with 0-4 $R^2$;

Y is substituted with 0-2 $R^1$ and is selected from the group:

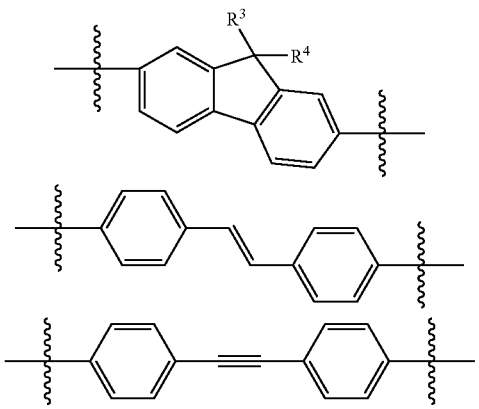

U and V, at each occurrence, are independently a bond, —CH=CH—, —CH=CH-phenylene-, or -phenylene-CH=CH—;

n is 1-20;

$R^1$ is independently hydroxy, F, Cl, Br, I, $C_1$-$C_6$ alkoxy, $C_1$-$C_{10}$ alkyl, or $C_1$-$C_4$ haloalkyl;

$R^2$ is independently amino, hydroxy, F, Cl, Br, I, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —$CO_2$H, or —$CO_2$ ($C_1$-$C_6$ alkyl); and $R^3$ and $R^4$, at each occurrence, are independently $C_1$-$C_{16}$ alkyl, $C_1$-$C_{10}$ haloalkyl, —($CH_2$)$_{1-9}$$CO_2$H, —($CH_2$)$_{1-9}$$CO_2$($C_1$-$C_6$ alkyl), —($CH_2CH_2$O)$_{1-6}$H, or —($CH_2CH_2$O)$_{1-6}$($C_1$-$C_6$ alkyl);

and, optionally, (b) a photoacid generator.

In another embodiment, the present invention provides a photosensitive composition comprising:

(a) a fluorophore-containing polymer comprising a unit selected from:

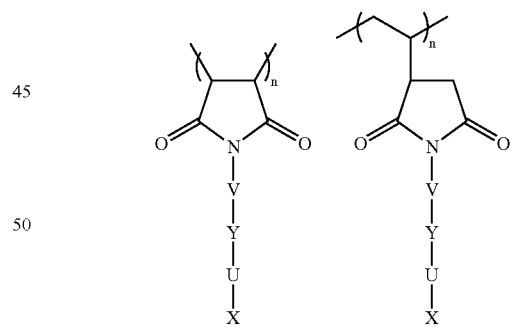

wherein Y is

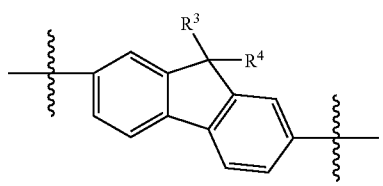

and substituted with 0-2 $R^1$;

and, optionally, (b) a photoacid generator.

In another embodiment, the present invention provides a photosensitive polymer composition comprising:

(a) a fluorophore-containing polymer comprising a unit selected from:

wherein X is selected from the group:
—NR$^5$, and

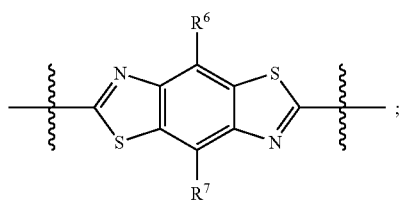

Y is substituted with 0-5 R$^1$ and is selected from the group:

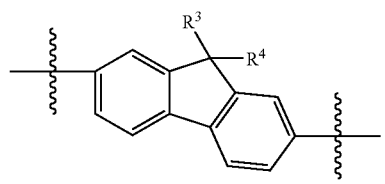

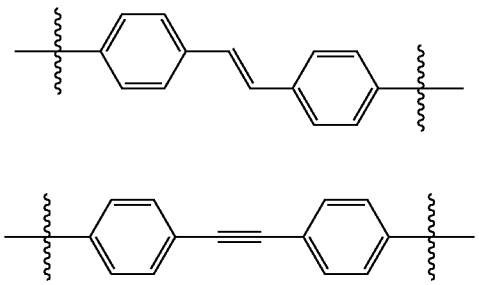

m is 1-50;

R$^1$ is independently amino, hydroxy, halogen, $C_1$-$C_6$ alkoxy, $C_1$-$C_{10}$ alkyl, $C_1$-$C_6$ haloalkyl, SH, SCH$_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), or —NH(C=S)—N($C_1$-$C_6$ alkyl)$_2$;

R$^3$ and R$^4$, at each occurrence, are independently $C_1$-$C_{16}$ alkyl, $C_1$-$C_{10}$ haloalkyl, —(CH$_2$)$_{1-9}$CO$_2$H, —(CH$_2$)$_{1-9}$CO$_2$($C_1$-$C_6$ alkyl), —(CH$_2$CH$_2$O)$_{1-6}$H, or —(CH$_2$CH$_2$O)$_{1-6}$($C_1$-$C_6$ alkyl);

R$^5$ is H, $C_1$-$C_{16}$ alkyl, $C_1$-$C_{10}$ haloalkyl, —CO($C_1$-$C_4$ alkyl), —(CH$_2$)$_{1-9}$CO$_2$H, —(CH$_2$)$_{1-9}$CO$_2$($C_1$-$C_6$ alkyl), $C_6$-$C_{14}$ aryl substituted with 0-5 R$^1$, or 5-14 membered heterocycle substituted with 0-5 R$^1$;

R$^6$ and R$^7$ at each occurrence, are independently H, $C_1$-$C_{16}$ alkyl, $C_1$-$C_{10}$ haloalkyl, —(CH$_2$)$_{1-9}$CO$_2$H, —(CH$_2$)$_{1-9}$CO$_2$($C_1$-$C_6$ alkyl), —(CH$_2$CH$_2$O)$_{1-6}$H, or —(CH$_2$CH$_2$O)$_{1-6}$($C_1$-$C_6$ alkyl);

and, (b) a photoacid generator.

In another embodiment, the present invention provides a photosensitive polymer composition, comprising:

(a) a fluorophore-containing polymer comprising a unit wherein Y is

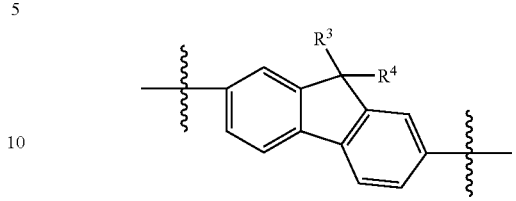

and substituted with 0-2 R$^1$;

and, (b) a photoacid generator.

In another embodiment, the present invention provides a novel compound of Formula II:

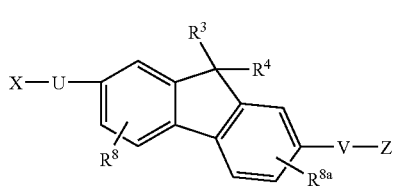

II wherein X is selected from the group:
—NH$_2$, —NH(aryl), —N(aryl)$_2$, 2-benzothiazolyl substituted with 0-4 R$^2$;

2-benzoxazolyl substituted with 0-4 R$^2$; and 2- or 4-pyridyl substituted with 0-4 R$^2$, and N-carbazolyl substituted with 0-4 R$^2$;

Z is H, X, CN, —N=C=S, NO$_2$, —NH(C=S)—O($C_1$-$C_6$ alkyl), —NH(C=S)—NH($C_1$-$C_6$ alkyl), —NH(C=S)—N($C_1$-$C_6$ alkyl)$_2$, —P(=O)(OH)$_2$, —P(=O)(OH)(O—$C_1$-$C_6$ alkyl), —P(=O)(O—$C_1$-$C_6$ alkyl)$_2$, —N-succinimidyl, $C_1$-$C_{20}$ alkyl substituted with 0-5 R$^1$, $C_1$-$C_{20}$ alkenyl substituted with 0-5 R$^1$, $C_1$-$C_{20}$ alkynyl substituted with 0-5 R$^1$, $C_6$-$C_{14}$ aryl substituted with 0-5 R$^1$, or 5-14 membered heterocycle substituted with 0-5 R$^1$;

U and V, at each occurrence, are independently a bond, —CH=CH—, —CH=CH-phenylene-, or -phenylene-CH=CH—;

R$^1$ is independently amino, hydroxy, halogen, $C_1$-$C_6$ alkoxy, $C_1$-$C_{10}$ alkyl, $C_1$-$C_6$ haloalkyl, SH, SCH$_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), or —NH(C=S)—N($C_1$-$C_6$ alkyl)$_2$;

R$^2$ is independently amino, hydroxy, halogen, $C_1$-$C_6$ alkoxy, $C_1$-$C_{10}$ alkyl, $C_1$-$C_6$ haloalkyl, SH, SCH$_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), —NH(C=S)—N($C_1$-$C_6$ alkyl)$_2$, —CO$_2$H, or —CO$_2$($C_1$-$C_6$ alkyl); and R$^3$ and R$^4$, at each occurrence, are independently $C_1$-$C_{16}$ alkyl, $C_1$-$C_{10}$ haloalkyl, —(CH$_2$)$_{1-9}$CO$_2$H, —(CH$_2$)$_{1-9}$CO$_2$($C_1$-$C_6$ alkyl), —(CH$_2$CH$_2$O)$_{1-6}$H, or —(CH$_2$CH$_2$O)$_{1-6}$($C_1$-$C_6$ alkyl);

R$^8$ and R$^{8a}$ are independently H, halogen, $C_1$-$C_6$ alkoxy, $C_1$-$C_{10}$ alkyl, or $C_1$-$C_6$ haloalkyl;

provided that when Z is H, NH$_2$, CN, NO$_2$, $C_1$-$C_8$ alkyl, then V is —CH=CH-phenylene-, or -phenylene-CH=CH—;

provided that when X is —N(phenyl)$_2$, R$^3$ and R$^4$ are ethyl, V is —CH═CH-phenylene-, Z is other than NO$_2$ or —P(═O)(OCH$_2$CH$_3$)$_2$;

provided that when X is —N(phenyl)$_2$, R$^3$ and R$^4$ are ethyl, hexyl, octyl, or decyl. V is a bond, Z is other than —N(phenyl)$_2$ or 2-benzothiazolyl;

provided that when X is —N(4-methoxyphenyl)$_2$, R$^3$ and R$^4$ are decyl, V is a bond, Z is other than 2-benzothiazolyl.

In another embodiment, the present invention provides the use of a photosensitive (polymer) composition of the present invention for WORM optical data storage with two-photon photoacid generation induced recording using red to near infra-red laser radiation, in single or three-dimensional multilayer structures.

In another embodiment, the present invention provides the use of a photosensitive (polymer) composition of the present invention for WORM optical data storage with two-photon fluorescent readout using red to near infra-red laser radiation, in single or three-dimensional multilayer structures.

In another embodiment, the present invention provides a WORM optical data storage device comprising:
 (a) a disk structure suitable for structurally supporting a polymer film;
 (b) said polymer film containing about 0.01 to 5.0 wt % of the fluorophore and about 0.5 to about 20.0 wt % of PAG, relative to the polymer; and,
 (c) said polymer film supported by said disk structure.

In another embodiment, the present invention provides a WORM optical data storage device wherein said polymer film contains about 0.1 to 0.9 wt % of the fluorophore and about 4.0 to 9.0 wt % of PAG, relative to the polymer.

In another embodiment, the present invention provides a WORM optical data storage device comprising:
 (a) a disk structure suitable for structurally supporting a polymer film;
 (b) said polymer film containing about 0.01 to 5.0 wt % of the fluorophore and about 0.5 to about 20.0 wt % of PAG, relative to the polymer and supported by said disk structure; and,
 (c) said polymer film irradiated to decrease the fluorescence concentration of the neutral fluorophore and increase the fluorescence of the monoprotonated fluorophore supported by said disk structure whereby the resulting stored optical information can be recovered via multichannel readout.

In another embodiment, the present invention provides a compound of Formula III:

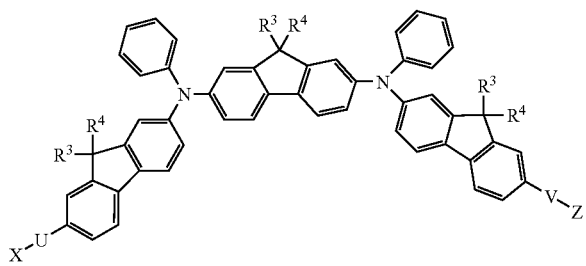

III wherein X is selected from the group:
 —NH$_2$, —NH(aryl), —N(aryl)$_2$, 2-benzothiazolyl substituted with 0-4 R$^2$;
 2-benzoxazolyl substituted with 0-4 R$^2$; and 2- or 4-pyridyl substituted with 0-4 R$^2$, and N-carbazolyl substituted with 0-4 R$^2$;

Z is H, X, CN, —N═C═S, NO$_2$, —NH(C═S)—O(C$_1$-C$_6$ alkyl), —NH(C═S)—NH(C$_1$-C$_6$ alkyl), —NH(C═S)—N(C$_1$-C$_6$ alkyl)$_2$, —P(═O)(OH)$_2$, —P(═O)(OH)(O—C$_1$-C$_6$ alkyl), —P(═O)(O—C$_1$-C$_6$ alkyl)$_2$, —N-succinimidyl, C$_1$-C$_{20}$ alkyl substituted with 0-5 R$^1$, C$_1$-C$_{20}$ alkenyl substituted with 0-5 R$^1$, C$_1$-C$_{20}$ alkynyl substituted with 0-5 R$^1$, C$_6$-C$_{14}$ aryl substituted with 0-5 R$^1$, or 5-14 membered heterocycle substituted with 0-5 R$^1$;

U and V, at each occurrence, are independently a bond, —CH═CH—, —CH═CH-phenylene-, or -phenylene-CH═CH—;

R$^1$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N═C═S, —NH(C═S)—O(C$_1$-C$_6$ alkyl), —NH(C═S)—NH (C$_1$-C$_6$ alkyl), or —NH(C═S)—N(C$_1$-C$_6$ alkyl)$_2$;

R$^2$ is independently amino, hydroxy, halogen, C$_1$-C$_6$ alkoxy, C$_1$-C$_{10}$ alkyl, C$_1$-C$_6$ haloalkyl, SH, SCH$_3$, —NH(C$_1$-C$_6$ alkyl), —N(C$_1$-C$_6$ alkyl)$_2$, —NH(aryl), —N(aryl)$_2$, —NHCO(C$_1$-C$_4$ alkyl), —N═C═S, —NH(C═S)—O(C$_1$-C$_6$ alkyl), —NH(C═S)—NH (C$_1$-C$_6$ alkyl), —NH(C═S)—N(C$_1$-C$_6$ alkyl)$_2$, —CO$_2$H, or —CO$_2$(C$_1$-C$_6$ alkyl); and R$^3$ and R$^4$, at each occurrence, are independently C$_1$-C$_{16}$ alkyl, C$_1$-C$_{10}$ haloalkyl, —(CH$_2$)$_{1-9}$CO$_2$H, —(CH$_2$)$_{1-9}$CO$_2$(C$_1$-C$_6$ alkyl), —(CH$_2$CH$_2$O)$_{1-6}$H, or —(CH$_2$CH$_2$O)$_{1-6}$(C$_1$-C$_6$ alkyl).

In another embodiment, the present invention presents novel fluorophore compounds of the following formula:

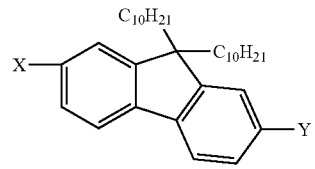

wherein X is selected from the group:
 —NH$_2$, —NH(phenyl), —N(phenyl)$_2$, 2-thiazolyl substituted with 0-2 R$^2$; 2-oxazolyl substituted with 0-2 R$^2$; 2-benzothiazolyl substituted with 0-4 R$^2$; 2-benzoxazolyl substituted with 0-4 R$^2$; 2- or 4-pyridyl substituted with 0-4 R$^2$, and N-carbazolyl substituted with 0-4 R$^2$;

wherein Z is H, I, Br, Cl, CN, —N═C═S, NO$_2$, —NH(C═S)—O(C$_1$-C$_6$ alkyl), —NH(C═S)—NH(C$_1$-C$_6$ alkyl), —NH(C═S)—N(C$_1$-C$_6$ alkyl)$_2$, —P(═O)(OH)$_2$, —P(═O)(OH)(O—C$_1$-C$_6$ alkyl), —P(═O)(O—C$_1$-C$_6$ alkyl)$_2$, —N-succinimidyl, C$_1$-C$_{20}$ alkyl substituted with 0-5 R$^1$, C$_1$-C$_{20}$ alkenyl substituted with 0-5 R$^1$, C$_1$-C$_{20}$ alkynyl substituted with 0-5 R$^1$, C$_6$-C$_{14}$ aryl substituted with 0-5 R$^1$, or 5-14 membered heterocycle substituted with 0-5 R$^1$;

Illustrative compounds include:
7-benzothiazol-2-yl-9,9-didecylfluoren-2-ylamide;
7-cyano-9,9-didecylfluoren-2-ylamine;
2-(9,9-didecyl-7-cyanofluorene-2-yl)diphenylamine;
9,9-Didecyl-7-iodofluoren-2-yl)diphenylamine; and, 9,9-Didecyl-2,7-bis[phenyl-(9,9-didecyl-2-[N,N-diphenylamino]-fluorenyl)aminofluorene.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

It would be useful to discuss the meanings of some words used herein and their applications before discussing FIGS. 1-22 including— fluorophore: chemical structure that absorbs light followed by emission of light of a different wavelength;

PAG: photoacid generator; chemical substance that absorbs light and undergoes reaction to produce protons (acid);

single-photon absorption: process whereby a molecule interacts with light and absorption of one photon causes and electronic excitation;

two-photon absorption: process whereby a molecule interacts with light and undergoes simultaneous or near-simultaneous absorption of two photons of approximately one-half the energy required to cause an electronic excitation, the energies of the two photons are essentially summed, producing an electronic excitation analogous to that obtained via single-photon absorption;

photolysis: chemical reaction induced by absorption of light (light-induced chemical reaction);

photochromism: color change caused in a material by irradiation with light two-photon induced photochromism: color change caused by a material undergoing simultaneous absorption of two photons;

upconverted fluorescence: shorter wavelength light emitted by a material that was irradiated with longer wavelength light;

photobleaching: chemical change caused by irradiation with light causing a decrease in the absorption of the material at the original wavelength of irradiation;

protonation: chemical substance that reacted with protons (one or more equivalents of acid);

monoprotonated: chemical substance that reacted with one proton (one equivalent of acid);

diprotonated: chemical substance that reacted with two proton (two equivalents of acid);

fs represents femtoseconds;

ps represents picoseconds; and, ns represents nanoseconds.

The discovery that it is possible to photoinduce protonation of fluorene dye 1 in liquid solution and poly mer thin films by conventional UV or visible light exposure or two-photon irradiation with red to near-IR laser irradiation (FIG. 1), and subsequent 3-D imaging of multilayer polymer films via two-photon fluorescence imaging, makes possible the production of a write-once read-many (WORM) enhanced high density three-dimensional optical data storage system. Thus, the invention relates to image formation via photoinduced fluorescence changes in a polymeric medium with two-photon fluorescence readout of a multilayer structure. Specifically, organic fluorescent dyes that contain a basic amine functionality that possess high two-photon absorptivity can react with protons produced by a photoacid generator upon exposure to a broad-band UV or visible light source or ultrafast near-IR laser irradiation (femtosecond, picosecond or nanosecond time scale). Subsequently, detailed solution studies demonstrate the formation of both monoprotonated and diprotonated species upon irradiation, each resulting in distinctly different absorption and fluorescence properties. The fluorescence of the original neutral, fluorophore was reduced upon monoprotonation, leading to a concomitant increase in fluorescence at longer wavelengths due to the monoprotonated form. Experiments in polymer films demonstrate that the changes in fluorescence properties of the fluorophores can be employed for a write-once read-many (WORM) data storage medium with two-photon fluorescent readout. Two-channel two-photon fluorescence imaging provided both "positive" and "negative" image readout capability.

Materials

Acid-Sensitive Organic Two-Photon Fluorescent Dyes

Although the two-photon absorbing fluorophore, 7-benzothiazoly-9,9-didecyl-2,2-(N,N-diphenylamino)fluorene, designated herein as fluorene 1, is the preferred organic fluorescent dye with high two-photon absorptivity of this invention, there are several additional useful organic fluorescent dyes whose spectral properties change appropriately upon exposure to acid and possess high two-photon absorptivity including those with the general structures shown in Formula I:

wherein X is selected from the group:

—$NH_2$, —$NH(C_1$-$C_6$ alkyl), —$N(C_1$-$C_6$ alkyl)$_2$, —NH (aryl), —$N(aryl)_2$, —$NHCO(C_1$-$C_4$ alkyl), 2-thiazolyl substituted with 0-2 $R^2$; 2-oxazolyl substituted with 0-2 $R^2$; 2-benzothiazolyl substituted with 0-4 $R^2$;

2-benzoxazolyl substituted with 0-4 $R^2$; and 2- or 4-pyridyl substituted with 0-4 $R^2$, and N-carbazolyl substituted with 0-4 $R^2$;

Y is substituted with 0-5 $R^1$ and is selected from the group:

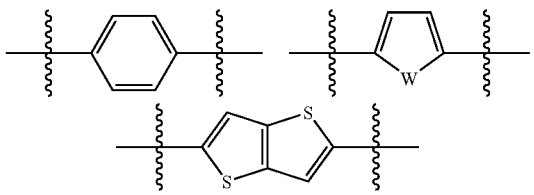

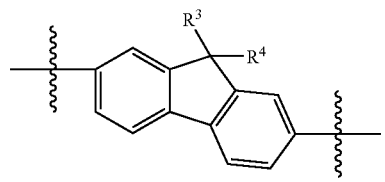

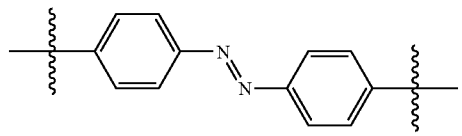

-continued

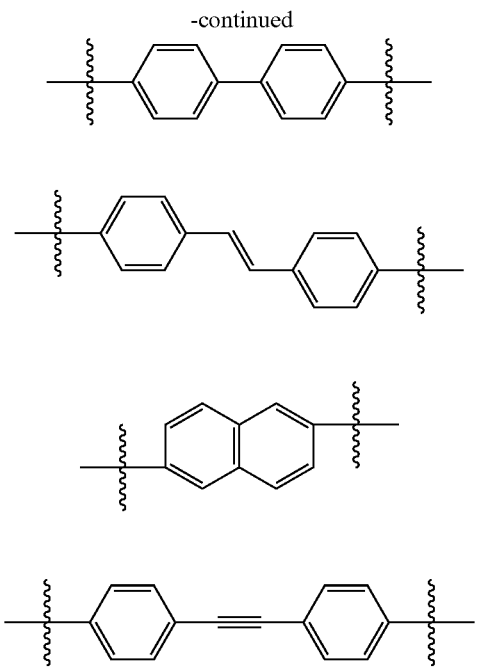

W is O, S, NH or N($C_1$-$C_6$ alkyl);

Z is H, X, CN, —N=C=S, $NO_2$, —NH(C=S)—O($C_1$-$C_6$ alkyl), —NH(C=S)—NH($C_1$-$C_6$ alkyl), —NH(C=S)—N($C_1$-$C_6$ alkyl)$_2$, —P(=O)(OH)$_2$, —P(=O)(OH)(O—$C_1$-$C_6$ alkyl), —P(=O)(O—$C_1$-$C_6$ alkyl)$_2$, —N-succinimidyl, $C_1$-$C_{20}$ alkyl substituted with 0-5 $R^1$, $C_1$-$C_{20}$ alkenyl substituted with 0-5 $R^1$, $C_1$-$C_{20}$ alkynyl substituted with 0-5 $R^1$, $C_6$-$C_{14}$ aryl substituted with 0-5 $R^1$, or 5-14 membered heterocycle substituted with 0-5 $R^1$;

U and V, at each occurrence, are independently a bond, —CH=CH—, —CH=CH-phenylene-, or -phenylene-CH=CH—;

$R^1$ is independently amino, hydroxy, halogen, $C_1$-$C_6$ alkoxy, $C_1$-$C_{10}$ alkyl, $C_1$-$C_6$ haloalkyl, SH, $SCH_3$, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), or —NH(C=S)—N($C_1$-$C_6$ alkyl)$_2$;

$R^2$ is independently amino, hydroxy, halogen, $C_1$-$C_6$ alkoxy, $C_1$-$C_{10}$alkyl, $C_1$-$C_6$ haloalkyl, SH, SCH, —NH($C_1$-$C_6$ alkyl), —N($C_1$-$C_6$ alkyl)$_2$, —NH(aryl), —N(aryl)$_2$, —NHCO($C_1$-$C_4$ alkyl), —N=C=S, —NH(C=S)—O($C_1$-$C_6$ alkyl), —NH(C=S)—NH($C_1$-$C_6$ alkyl), —NH(C=S)—N($C_1$-$C_6$ alkyl)$_2$, —$CO_2$H, or —$CO_2$($C_1$-$C_6$ alkyl); and $R^3$ and $R^4$, at each occurrence, are independently $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl), —$(CH_2CH_2O)_{1-6}H$, or —$(CH_2CH_2O)_{1-6}(C_1$-$C_6$ alkyl).

Specifically these compounds contain a basic nitrogen atom that can readily undergo protonation. Further, the spectral properties (absorption and fluorescence) must be distinctly different for the unprotonated and protonated forms such that they can be easily, resulting in high contrast between protonated (herein referred to as exposed) and unprotonated (herein referred to as unexposed) materials. In addition, the dyes must be capable of undergoing two-photon absorption and be subsequently accompanied by efficient upconverted fluorescence emission. Representative examples of such fluorophores prepared are summarized below in which $R^3$ and $R^4$, are $C_1$-$C_{16}$ alkyl, $C_1$-$C_{10}$ haloalkyl, —$(CH_2)_{1-9}CO_2H$, —$(CH_2)_{1-9}CO_2(C_1$-$C_6$ alkyl), or —$(CH_2CH_2O)_{1-6}H$, or —$(CH_2CH_2O)_{1-6}(C_1$-$C_6$ alkyl).

1

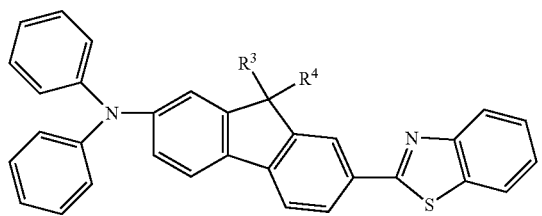

4

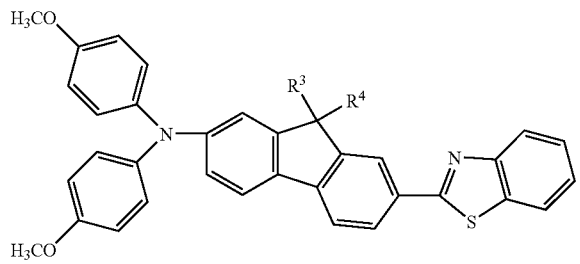

5

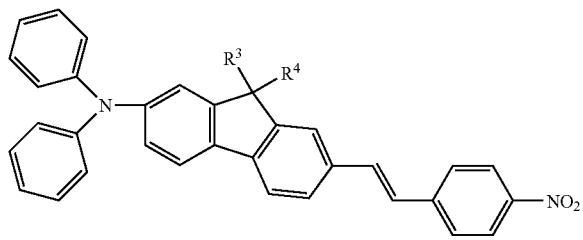

6

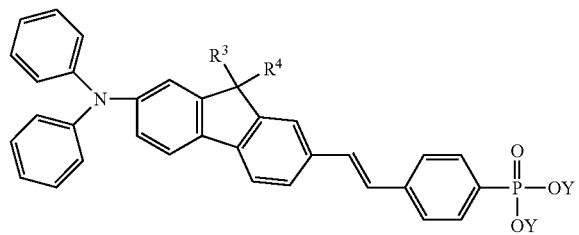

Y = H, $C_2H_5$

-continued
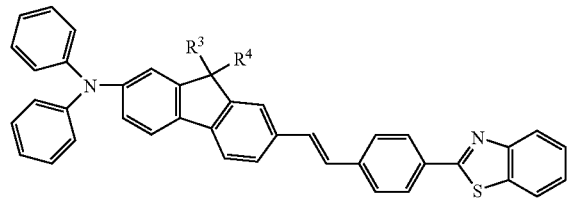 7
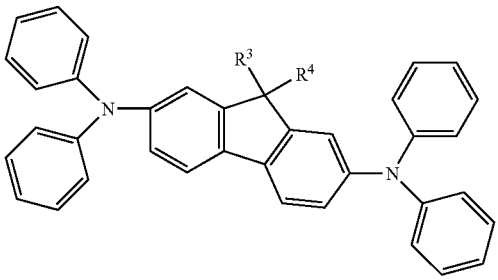 8
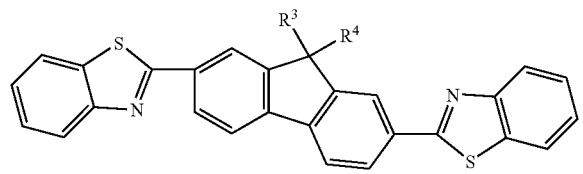 9
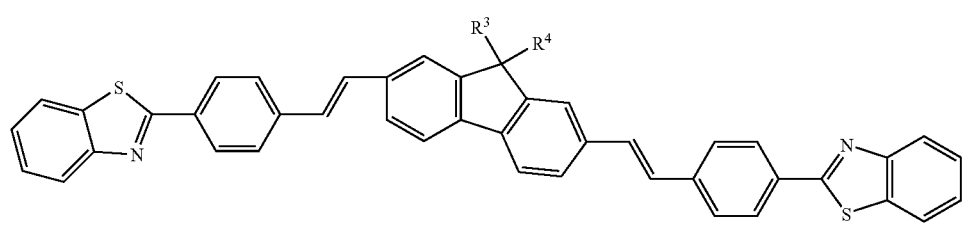 10
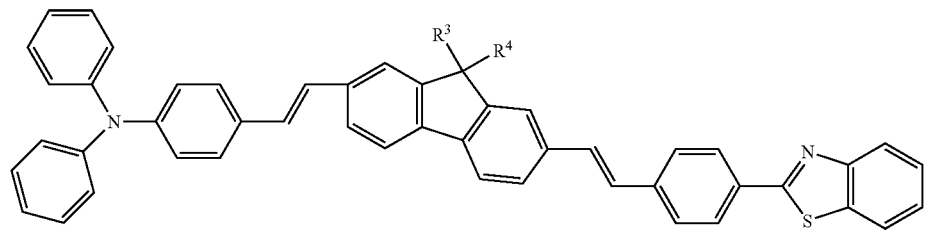 11
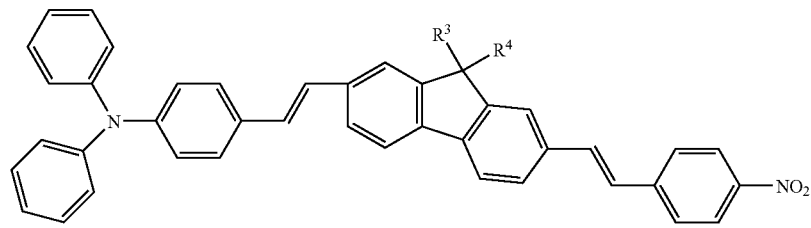 12
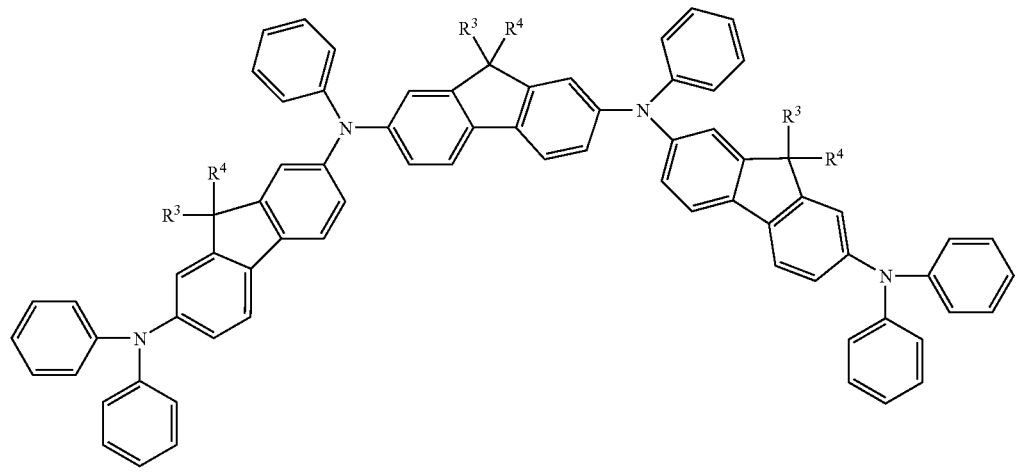 13

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable occurs more than one time in any constituent or in any formula, its definition on each occurrence is independent of its definition at every other occurrence. Thus, for example, if a group is shown to be substituted with 0-2 $R^1$, then said group may optionally be substituted with up to two $R^1$ and $R^1$ at each occurrence is selected independently from the defined list of possible $R^1$.

When a bond to a substitutent is shown to cross the bond connecting two atoms in a ring, then such substitutent may be bonded to any atom on the ring. When a bond joining a substitutent to another group is not specifically shown or the atom in such other group to which the bond joins is not specifically shown, then such substitutent may form a bond with any atom on such other group.

When a substitutent is listed without indicating the atom via which such substitutent is bonded to the rest of the compound of Formula I, then such substituent may be bonded via any atom in such substitutent. For example, when the substitutent is piperidinyl, morpholinyl, or pyridinyl, unless specified otherwise, said piperidinyl, morpholinyl, or pyridinyl group may be bonded to the rest of the compound of Formula (I) via any atom in such piperidinyl, morpholinyl, or pyridinyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an effective polymer material.

The term "substituted", as used herein, means that any one or more hydrogen on the designated atom is replaced with a selection from the indicated group, provided that the designated atom's normal valency is not exceeded, and that the substitution results in a stable compound.

As used herein, "alkyl" or "alkylene" is intended to include both branched and straight-chain saturated aliphatic hydrocarbon groups having the specified number of carbon atoms; for example, "$C_1$-$C_{10}$ alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, pentyl, hexyl, heptyl, octyl, nonyl and decyl.

"Alkenyl" or "alkenylene" is intended to include hydrocarbon chains of either a straight or branched configuration, having the specified number of carbon atoms, and one or more unsaturated carbon-carbon bonds which may occur in any stable point along the chain, such as ethenyl, propenyl, 1-butenyl, 2-butenyl and the like.

"Alkynyl" or "alkynylene" is intended to include hydrocarbon chains of either a straight or branched configuration, having the specified number of carbon atoms, and one or more carbon-carbon triple bonds which may occur in any stable point along the chain, such as ethynyl, propynyl, 1-butynyl, 2-butynyl and the like.

The term "haloalkyl" is intended to include both branched and straight-chain saturated aliphatic hydrocarbon groups having the specified number of carbon atoms, substituted independently with 1 or more halogens (for example—$C_vF_w$ where v=1 to 3 and w=1 to (2v+1)), such as, but not limited to, —$CH_2F$, —$CHF_2$, —$CF_3$, —$CH_2CF_3$, —$CF_2CF_3$, —$CH(CF_3)_2$ and the like.

As used herein, "alkyloxy" or "alkoxy" represents an alkyl group of indicated number of carbon atoms attached through an oxygen bridge, for example methoxy, ethoxy, propoxy, i-propoxy, butoxy, i-butoxy, s-butoxy and t-butoxy. The term "aryloxy" is intended to mean phenyl or naphthyl attached through an oxygen bridge.

The term "cycloalkyl" is intended to include saturated ring groups having the specified number of carbon atoms, including mono-, bi-, or poly-cyclic ring systems, such as cyclopropyl (c-Pr), cyclobut), cyclobutyl(c-Bu), cyclopentyl, cyclohexyl, cycloheptyl, cyclooctyl, [3.3.0]bicyclooctyl, [2.2.2]bicyclooctyl, adamantyl and so forth. More specifically, "bicycloalkyl" is intended to include saturated bicyclic ring groups having the specified number of carbon atoms, such as [3.3.3]bicyclooctyl, [4.3.0]bicyclononyl, [4.4.0]bicyclodecyl (decalin), [2.2.2]bicyclooctyl, and so forth.

Additionally, the terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo.

As used herein, "aryl" or "aromatic residue" is intended to mean 6 to 14 membered monocyclic, bicyclic or tricyclic unsaturated carbon ring, for example phenyl, biphenyl, naphthyl or fluorenyl. As used herein "aryl" is optionally substituted with 0-5 groups independently selected from amino, hydroxy, halogen, $C_1$-$C_6$ alkoxy, $C_1$-$C_{10}$ alkyl, $C_1$-$C_6$ haloalkyl, $SCH_3$, —$NH(C_1$-$C_6$ alkyl), —$N(C_1$-$C_6$ alkyl)$_2$, —NH(aryl), —N(aryl)$_2$, —NHCO($C_1$-$C_4$ alkyl).

The term "arylalkyl" represents an aryl group attached through an alkyl bridge having the specified number of carbon atoms.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocycles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, benzoxazolyl, benzothiazolyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, .beta.-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, 1,4-benzoxazine, and 8-oxa-3-azabicyclo[3,2,1]octane. Preferred heterocyclic rings are pyridinyl, furanyl, thiazolyl, thienyl, pyrrolyl, pyrazolyl, triazolyl, imidazolyl, benzofuranyl, benzothiophenyl, benzoxazolyl, benzothiazolyl, indolyl, indolinyl, quinolinyl, isoquinolinyl, tetrahydroisoquinolinyl, isoxazolyl, isoxazolinyl, benzyimdazolyl, piperidinyl, tetrahydrofuranyl, pyranyl, pyrimidinyl, 3H-indolyl, pyrrolidinyl, morpholinyl, piperazinyl and carbazole. Also included are fused ring and spiro compounds containing, for example, the above heterocycles.

As used herein, the term "heteroaryl" refers to aromatic heterocyclic groups. Such heteroaryl groups are preferably 5-6 membered monocylic groups or 8-10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzoxazolyl, benzothiazolyl, benzimidazolyl, quinolinyl, or isoquinolinyl.

As used herein. "carbonyl" means a carbon double bonded to oxygen and additionally substituted with two groups through single bonds; "carbonyloxy" means a carbon double bonded to oxygen and additionally bonded through single bonds to two groups, one of which is an oxygen.

Photoacid Generators (PAG)

Suitable photoacid generators are characterized by their ability to absorb light and undergo photochemical reaction to produce one or more protons (H+) or acid in the absence or presence of sensitizers or coinitiators such as isopropylthioxanthone (ITX). In addition to the compounds of the present invention, the photoresist compositions of the invention contain a PAG. The invention is not limited to the use of any specific PAG or combination of PAG's, that is the benefits of the invention may be achieved using various photosensitive acid generators known in the art. Examples of suitable photosensitive acid generators include onium salts such as triaryl sulfonium hexafluoroantimonate, diaryliodonium hexafluoroantimonate, hexafluoroarsenates, triflates (e.g. triphenylsulfonium triflate, bis(t-butyl phenyl) iodonium triflate), substituted aryl sulfonates such as pyrogallols (e.g. trimesylate of pyrogallol or tris(sulfonate) of pyrogallol), sulfonate esters of hydroxyimides, N-sulfonyloxynaphthalimides (N-camphorsulfonyloxynaphthalimide, N-pentafluorobenzenesulfonyloxynaphthalimide), .alpha.-.alpha.'bis-sulfonyl diazomethanes, sulfonate esters of nitro-substituted benzyl alcohols, naphthoquinone-4-diazides, alkyl disulfones and mixtures thereof.

Binder Polymers

Polymers can be used that do not absorb the laser light being used for data writing or reading. The polymer serves to create an amorphous or mostly amorphous material that can be coated on surfaces or formed into bulk objects. The glass transition temperature of the polymer must be above 30° C. and it must be either soluble in solvents for spin coating or solution casting or be melt processable or both. Examples include but are not limited to polystryene and its derivatives, polyacrylates, polymethacrylates, polycarbonates, polyurethanes, polysiloxanes, nylons, and polyesters.

EXPERIMENTAL

Belfield et al. reported the synthesis and characterization of organic fluorescent dyes with high two-photon absorptivity (J. Phys. Org. Chem. 2000, 13, 837; J. Org. Chem. 2000, 65, 4475; Org. Lett. 1999, 1, 1575).

The photoacid generator, CD1010 (a triarylsulfonium hexafluoroantimonate salt as 50 wt % in propylene carbonate), was purchased from Sartomer and used as received. The synthesis and characterization of the two-photon absorbing fluorophore, 7-benzothiazoly-9,9-didecyl-2,2-(N, N-diphenylamino)fluorene, was described previously by Belfield et al. (J. Org. Chem. 2000, 65, 4475). Polystyrene (PS) (molecular weight 35,000) was purchased from Waters Associates and used directly. Phosphorylated poly (VBC-co-MMA) was prepared as previously reported (Belfield, K. D. and Wang, J. J. Polym. Sci., Polym. Chem. Ed. 1995, 33; 1235). Acetonitrile (ACN), 1,4-dioxane, and $CH_2Cl_2$ (HPLC or spectrophotometric grades) were purchased from Sigma-Aldrich and were used as received. Various masks were used during the photoexposure of prepared polymer films, including TEM grids (nickel square and hexagonal mesh grids from Polysciences), glass resolution targets (negative slide with the 1951 USAF test pattern from Edmund Scientific), and photolithographic waveguide masks (from PPM Photomask, Inc).

Example 1

Synthesis of 7-benzothiazol-2-yl-9,9-didecylfluoren-2-ylamide (16)

In a 50 mL 3-neck reaction flask, fitted with a mechanical stirrer, $N_2$ inlet, and stopper, was placed 2,7-dicyano-9,9-didecylfluorene (0.68 g, 1.36 mmol), 2-aminothiophenol (0.34 g, 2.73 mmol) and 5.38 g of polyphosphoric acid (PPA). 2,7-Dicyano-9,9-didecylfluorene was prepared in two steps from fluorene (purchased from Aldrich) by reaction first with bromodecane, then CuCN. The reaction was slowly heated to 80° C., by which time complete dissolution had occurred. On stirring for 5 h at 80° C. the temperature was raised to 120° C. and stirred for 24 h, at which time the reaction mixture turned yellow-orange. The temperature was raised to 140° C. for 40 h. The reaction mixture was cooled and poured into water to precipitate the yellow solid. The crude product was then stirred in 50% ammonium hydroxide ($NH_4OH$) for 1 h, filtered, and washed with water. It was dried, and purified by recristallization using (60:40 hexanes/$CH_2Cl_2$) and column chromatographic on silica gel (50:50 hexanes/$CH_2Cl_2$) obtaining 0.5 g of white solid (51.2% yd, mp=138-139.5° C.). Anal Calcd for $C_{41}H_{56}N_2O_2S$: C, 76.82%; H, 8.8%; N, 4.37%; O, 4.99%; S, 5.0%. Found: C, 76.83%; 8.75%; N, 4.41%; O, 4.99%; S, 5.0%. $^1H$ NMR (300 MHz, $CDCl_3$) δ: 8.12 (dd, 3H), 7.89 (m, 5H), 7.51 (t, 1H), 7.39 (t, 1H), 2.14 (m, 4H), 1.10 (m, 28H), 0.78 (t, 6H), 0.58 (bs, 4H). $^{13}C$ NMR (300 MHz, $CDCl_3$) δ: 169.8, 168.4, 154.4, 152.7, 152.1, 144.2, 142.9, 135.2, 133.5, 132.6, 127.4, 126.6, 126.5, 125.4, 123.3, 122.5, 121.8, 121.8, 121.1, 120.4, 56.0, 40.4, 32.0, 30.1, 29.7, 29.5, 29.4, 24.0, 22.8, 14.3. FT-IR (KBr, $cm^{-1}$): 3500 (vOH, water), 2920, 2851 (valCH), 1655 (vC=O, amide I), 1616 (δ NH, amide II), 1577 (vC=N).

Example 2

Synthesis of 7-cyano-9,9-didecylfluoren-2-ylamine (18)

7-Cyano-9,9-didecyl-2-nitrofluorene (0.88 g, 1.87 mmol) was dissolved in a mixture of THF (3 mL) and EtOH (8 mL) at room temperature. 7-Cyano-9,9-didecyl-2-nitrofluorene was prepared in three steps from fluorene (purchased from Aldrich) by reaction first Nitric and sulfuric acid, then bromodecane, and finally CuCN. To this was added graphite, and the mixture was degassed under vacuum and $N_2$. The mixture was heated to 90° C. under $N_2$ and hydrazine hydrate (1.05 g, 32.89 mmol) was added dropwise via syringe. TLC analysis using (60:40) hexanes/$CH_2Cl_2$, indicated reduction was complete after 48 h. The reaction mixture was filtered, concentrated, and the resulting yellow-orange oil was passed through a Si gel column, using (70:30) hexanes/$CH_2Cl_2$, providing 0.62 g of yellow solid (75.4% yd; mp=46-47° C.). Anal. Calcd for $C_{34}H_{50}N_2$: C, 83.99%; H, 10.35; N, 5.75%. Found: C, 83.84%; H, 10.50%; N, 5.73%. $^1H$ NMR (300 MHz, $CDCl_3$) δ: 7.5 (t, 4H), 6.6 (d, 2H), 3.8 (bs, 2H), 1.87 (m, 4H), 1.1 (m, 28H), 0.85 (t, 6H), 0.54 (m, 4H). $^{13}C$ NMR (300 MHz, $CDCl_3$) δ: 148.9, 145.6, 142.9, 141.5, 126.6, 125.5, 121.2, 117.1, 115.6, 113.8, 109.5, 104.4, 102.9, 50.3, 35.6, 27.1, 26.8, 25.2, 24.8, 24.7, 24.5, 18.9, 17.9, 9.3. FT-IR (KBr, $cm^{-1}$): 3479, 3379 ($vNH_2$), 2923, 2853, (valCH), 2221 (vC≡N), 1603 (vAr C=C).

Example 3

Synthesis of 2-(9,9-didecyl-7-cyanofluorene-2yl)diphenylamine (19)

7-Cyano-9,9-didecylfluoren-2-ylamine (0.4 g, 0.9 mmol) was subjected to an Ullmann condensation reaction with iodobenzene (0.92 g, 4.5 mmol) at 180° C. for 48 h. The 2-amino-7-cyano-9,9-didecylfluorene was prepared directly from 7-cyano-9,9-didecyl-2-nitrofluorene (reported in the previous example) by reduction using graphite and hydrazine hydrate. The synthetic procedures were performed in analogy to the procedures given for 3. A bright yellow viscous oil was obtained after column chromatographic purification (0.48 g, 89% yd). Anal. Calcd for $C_{46}H_{58}N_2$: C, 86.47%; H, 9.14%; N, 4.38%. Found: C, 86.72%; H, 9.14%; N, 4.38%. $^1$H NMR (300 MHz, $CDCl_3$) δ: 7.57 (m, 4H), 7.25 (t, 4H), 7.08 (m, 8H), 1.84 (m, 4H), 1.11 (m, 28H), 0.88 (t, 6H), 0.60 (m, 4H). $^{13}$C NMR (300 MHz, $CDCl_3$) δ: 150.0, 148.3, 146.1, 144.7, 142.8, 130.7, 128.6, 126.5, 123.3, 121.6, 120.3, 120.0, 118.7, 116.5, 115.2, 105.8, 52.5, 37.1, 29.0, 27.0, 26.7, 26.7, 26.4, 21.0, 19.8, 11.3. FT-IR (KBr, cm$^{-1}$): 3064, 3036 (vArCH), 2926, 2854 (valCH), 2223 (vC≡N), 1595 (vArC=C).

Example 4

Synthesis of 7-cyano-9,9-didecylfluorene-2-(4,4'-dicyanodiphenylamine) (20)

In a two-neck round-bottom flasks, fitted with a $N_2$ inlet, condenser and stir bar, stopper, was placed 7-cyano-9,9-didecylfluoren-2-ylamine (0.26 g, 0.60 mmol) (described in the example above), 4-fluorobenzonitrile (0.07 g, 0.66 mmol), finely ground cesium fluoride (0.25 g, 1.64 mmol), and (3 mL) DMSO. The temperature was then gradually raised to 100° C. for 13 h, and 145° C. for 72 h. The brown solution was cooled and poured over ice. The organic layer was extracted with $CH_2Cl_2$, washed with water, dried and concentrated to obtain a yellow-brown oil. Purification was accomplished by column chromatography using (40:60 hexanes/$CH_2Cl_2$), providing 0.12 g of light brown solid (30% yd). Anal. Calcd for $C_{48}H_{56}N_4$: C, 83.67%; H, 8.19%; N, 8.13%. Found: C, 83.0%; H, 8.25%; N, 7.90%. $^1$H NMR (300 MHz, $CDCl_3$) δ: 7.75 (d, 2H), 7.64 (d, 1H), 7.60 (s, 1H), 7.5 (d, 4H), 7.16 (t, 6H), 1.92 (m, 4H), 1.1 (m, 28H), 0.88 (t, 6H), 0.58 (bs, 4H). $^{13}$C NMR (300 MHz, $CDCl_3$) δ: 154.0, 151.6, 150.2, 144.6, 137.5, 133.8, 131.8, 126.7, 25.9, 123.3, 122.7, 121.4, 120.4, 119.8, 118.9, 110.4, 106.5, 55.9, 40.0, 32.0, 30.0, 29.7, 29.5, 29.5, 24.1, 22.8, 14.3. FT-IR (KBr, cm$^{-1}$): 3046 (vArCH), 2926, 2854 (valCH), 2224 (vC≡N), 1595 (vArC=C).

Example 5

Preparation of 7-Benzothiazol-2-yl-9,9-didecylfluoren-2-ylamine-modified poly(styrene-co-maleic Anhydride)

Poly(styrene-co-maleic anhydride) (2.8013 g) was dissolved in 2 mL tetrahydrofuran (THF). Distilled benzene (6 mL) was than added and the polymer solution was placed in a 25 mL two-necked round bottom flask fitted with a reflux condenser under $N_2$. While stirring 7-benzothiazole-2-yl-9,9-didecylfluorene-2-ylamine (Belfield et al. J. Org. Chem. 2000, 65, 4475) (0.470 g, 0.79 mmol, in 3.2 mL dry benzene) was added dropwise at r.t. to the reaction flask, resulting in a yellow-white precipitate upon addition. The reaction mixture was stirred for 1 hour, after which recrystallized $ZnCl_2$ (0.1208 g, 0.79 mmol) added in one portion, followed by heating to 80° C. Hexamethyldisilazane (HMDS) (0.25 mL, 1.18 mmol) in dry benzene (2.5 mL) was added slowly over a period of 30 minutes, and the reaction mixture was then refluxed for 80 hours. During the reflux period two additional portions of $ZnCl_2$ and HMDS were added at 24 and 48 hours, and the reaction followed by TLC. Upon completion, the reaction mixture was cooled to room temperature and poured into 0.5 N HCl (30 mL). The aqueous phase was extracted with ethyl acetate (3×25 mL), and the combined organic extracts were washed successively with 30 mL of saturated $NaHCO_3$ and brine solution and dried over $MgSO_4$. The solution was concentrated under reduced pressure and the crude polymer dissolved in a minimum amount of N,N-dimethylacetamide (DMAc) and precipitated in cold methanol twice then dried at reduced pressure. The final product was a bright yellow powder (36 wt % yield).

Example 6

7-Benzothiazol-2-yl-9,9-didecylfluoren-2-ylamine-Modified poly(ethylene-g-maleic Anhydride)

Poly(ethylene-g-maleic anhydride) (2.0052 g) was dissolved in a minimal amount of THF (12 mL) at 110° C. Distilled benzene (6 mL) was then added and the polymer solution placed into a 25 mL two-necked round bottom flask fitted with a reflux condenser under $N_2$. While stirring, 7-benzothiazole-2-yl-9,9-didecylfluorene-2-ylamine (0.05 g, 0.084 mmol, in 2.0 mL dry benzene) was added dropwise into the reaction flask. The reactants were stirred for 1 hour, then recrystallized $ZnCl_2$ (0.0114 g, 0.084 mmol) was added in one portion. The resulting reaction mixture was kept at 110° C. HMDS (0.03 mL, 0.1261 mmol) in dry benzene (0.3 mL) was added slowly over a period of 30 minutes. The reaction mixture was then refluxed for 164 hours, during which time it became a dark-brown color. During the reflux period, three additional portions of $ZnCl_2$ and HMDS were added at 24, 72, and 96 hours. TLC indicated the reaction was complete. The reaction mixture was cooled to room temperature and poured into 0.5 N HCl (110 mL). The aqueous phase was extracted with ethyl acetate (3×75 mL). The combined organic extracts were washed successively with 100 mL of saturated $NaHCO_3$ and brine, then dried over anhydrous $MgSO_4$. The solution was concentrated under reduced pressure. The polymer was dissolved in chloroform and precipitated in cold methanol twice, then dried at reduced pressure. The final product was a light green solid (52 wt % yield).

Example 7

General Procedure for the Ullmann Condensation. (9,9-Didecyl-7-iodofluoren-2-yl)-diphenylamine (15)

9,9-Didecyl-2,7-diiodofluorene (1.22 g, 1.7 mmol) (prepared as described in Belfield et al. Journal of Organic Chemistry, 2000) was dissolved in 6 mL of 1,2-dichlorobenzene at room temperature under $N_2$. To this were added K₂CO₃ (1.90 g, 13.77 mmol), 18-crown-6 (0.15 g, 0.61 mmol), and copper bronze (0.53 g, 8.32 mmol) at room temperature. Diphenylamine (0.30 g, 1.77 mmol) was added, and the reaction mixture was heated to 180° C. for 28 h. Upon completion, the brown mixture was filtered through a short silica gel plug and the yellow solution was concentrated resulting in a yellow-brown oil. The solvent 1,2-dichlorobenzene was removed under reduced pressure. Purification was accomplished by column chromatography using first (80:20) hexanes/CH$_2$Cl$_2$, followed by (90:10) hexanes/CH$_2$Cl$_2$, providing 0.44 g of light yellow oil (35%). $^1$H NMR (300 MHz, CDCl$_3$) δ: 7.61 (d, 2H), 7.52 (d, 1H), 7.35 (d, 1H), 7.22 (t, 5H), 7.12 (t, 5H), 7.03 (t, 2H), 1.81 (m, 4H), 1.11 (m, 28H), 0.86 (t, 6H), 0.62 (bs, 4H). $^{13}$C NMR (300 MHz, CDCl$_3$) δ: 153.3, 151.7, 148.1, 147.9, 140.8, 136.0, 135.0, 132.0, 129.4, 124.1, 123.6, 122.8, 121.0, 120.7, 119.2, 91.7, 55.4, 40.3, 32.1, 30.1, 29.8, 29.8, 29.5, 24.0, 22.9, 14.3. FT-IR (KBr, cm$^{-1}$): 3032 (vArCH), 2923, 2851 (valCH), (vArC=C).

Example 8

9,9-Didecyl-2,7-bis(N-phenylamino)fluorene (14) was Prepared by Reaction of 9,9-didecyl-2,7-diiodofluorene (Reported in Previous Example) with Aniline A yellow-brown oil was obtained after column chromatography purification using first n-hexanes/EtOAc (80:20), followed by n-hexanes/EtOAc (95:5) (0.40 g, 45% yd). UV-vis (ACN): λ$_{max}$=354 nm (250-400 nm). Anal. Calcd for C$_{45}$H$_{60}$N$_2$: C, 85.93%; H, 9.62%; N, 4.45%. Found: C, 85.91%; H, 9.62%; N, 4.45%. $^1$H NMR (300 MHz, CDCl$_3$) δ: 7.49 (s, 2H), 7.24 (d, 4H), 7.05 (d, 8H), 6.91 (s, 2H), 5.7 (bs, 2H0, 1.88 (bs, 4H), 1.11 (m, 28H), 0.84 (m, 10H). FT-IR (KBr, cm$^{-1}$): 3397 (vNH), 3031 (vArCH), 2923, 2855 (valCH), 1598 (vArC=C).

Example 9

Synthesis of 9,9-Didecyl-2,7-bis[phenyl-(9,9-didecyl-2-[N,N-diphenylamino]-fluorenyl)aminofluorene (13)

9,9-Didecyl-7-iodofluoren-2-yl)diphenylamine (15) (0.49 g, 0.66 mmol) was subjected to similar Ullmann condensation reaction with 9,9-didecyl-2,7-bis(phenylamino)fluorene (0.17 g, 0.27 mmol) to yield the desired product. (9,9-Didecyl-7-iodofluoren-2-yl)diphenylamine (15) was prepared by reaction of 9,9-didecyl-2,7-diiodofluorene (reported in Example 7) with one equivalent of diphenylamine. TLC analysis (60:40 hexanes/CH$_2$Cl$_2$) indicated condensation was complete after 4 days. The orange-brown oil was further purified by column chromatography on silica gel using first (70:30) hexanes/CH$_2$Cl$_2$, followed by (80:20) hexanes/CH$_2$Cl$_2$ resulting in 0.42 g of yellow solid (85% yd). Anal. Calcd for C$_{135}$H$_{174}$N$_4$: C, 87.51%; H, 9.46%; N, 3.02%. Found: C, 87.37; H, 9.53%; N, 3.02%. $^1$H NMR (300 MHz, C$_6$D$_6$) δ: 7.09 (d, 2H), 7.04 (s, 1H), 7.0 (dd, 5H), 6.93 (s, 1H), 6.85 (t, 6H), 6.73 (t, 6H), 6.53 (m, 3H), 1.33 (m, 4H), 0.87 (bd, 28H), 0.52 (bt, 10H). $^{13}$C NMR (300 MHz, C$_6$D$_6$) δ: 152.4, 148.5, 147.0, 136.6, 129.4, 124.2, 123.9, 120.2, 119.6, 119.1, 55.2, 40.3, 32.2, 30.4, 30.0, 29.8, 29.7, 29.6, 24.4, 22.9, 14.2. FT-IR (KBr, cm$^{-1}$): 3036 (vArCH), 2926, 2854 (valCH), 1593 (vArC=C).

Example 10

9,9-Didecyl-2,7-diphenylaminofluorene Polymer 9,9-Didecyl-2,7-diiodofluorene (0.157 g, 0.224 mmol) (prepared as described in Belfield et al. Journal of Organic Chemistry, 2000) and compound (14) (0.1414 g 0.224 mmol) were subjected to similar Ullmann condensation reaction to yield the polymer 5. After 12 days, TLC indicated that the condensation was complete. The dark brown oil was further purified by column chromatography on silica gel using first hexane/CH$_2$Cl$_2$ (70:30) followed by hexane/THF (85:15) providing a yellow solid. FT-IR (KBr, cm$^{-1}$): 2956, 2854 (valCH), 1465 (vArC=C). $^1$H NMR (300 MHz, C$_6$D$_6$) δ: 7.19 (d, 5H), 6.93 (d, 5H), 6.63 (s, 1H), 1.48 (bd, 4H), 0.85 (bm, 38H). $^{13}$C NMR (300 MHz, C$_6$D$_6$) δ: 151.17, 147.66, 145.83, 135.30, 128.30, 122.91, 122.39, 121.49, 119.04, 112.89, 59.10, 39.19, 31.00, 29.22, 28.82, 28.75, 28.61, 28.45, 23.32, 21.74, 13.03.

Example 11

Poly(benzo[1,2-d:4,5-d']bisthiazole-9,9-didecylfluorene)

Into a three-neck, 100 mL reaction flask were placed 2,7-dicyano-9,9-didecylfluorene (prepared as described in Example 1) (0.727 g, 0.0014 mol), 2,5-diamino-1,4-benzenethiol dihydrochloride (purchased from TCI America) (0.362 g, 0.0014 mol), and polyphosphoric acid (3.75 g). The reaction vessel was fitted with a mechanical stirrer, flushed with nitrogen and then heated to 45° C. under vacuum and stirred for 16 h. The temperature was then gradually raised to 60° C. for 4 h, and 100° C. for 2 h, resulting in the reaction mixture turning orange. The mixture was cooled to room temperature and 1.83 g of phosphorus pentoxide (P$_2$O$_5$) was added. The solution was then slowly heated to 100° C. and stirred for 16 h (reddish-orange solution), followed by heating to 130° C. for another 16 h, then at 145° C. for 6 h. The reaction mixture was immediately poured into water, resulting in a yellow-brown precipitate. The polymer was neutralized with NH$_4$OH (20%) and washed with water in a soxhlet extractor for 32 h. The polymer was dried and again washed with hexane in a soxhlet extractor, yielding a yellow solid (0.49 g, 53% yield).

Example 12

Synthesis of Fluorophore (10)

9,9-Didecyl-2,7-diiodo-fluorene (prepared as described in Belfield et al. Journal of Organic Chemistry, 2000) (1.40 g, 2.0 mmol), 2-(4-vinylphenyl)-benzothiazole (prepared by reaction of 2(4-iodophenyl)benzothiazole with tri-n-butylvinyltin (1.04 g, 4.4 mmol), Pd(OAc)$_2$ (45 mg, 0.20 mmol) and P(Tolyl)$_3$ (0.12 g, 0.40 mmol) were dissolved in 30 mL of a mixed solvent of degassed DMF-NEt$_3$ (5:1). The reaction mixture was refluxed for 48 h under nitrogen atmosphere. After confirmation of the disappearance of the starting diiolofluorene by TLC, the dark brown mixture was cooled to room temperature. The mixture was filtered and evaporated under reduced pressure. Distilled water was poured onto the residue, and the product was extracted with CH$_2$Cl$_2$. The extract was dried over MgSO$_4$, and the solvent was removed under reduced pressure. The residue was chromatographed on a silica gel column using mixed eluent of n-hexane/ethyl acetate (10:1) to give 0.40 g (22% yield) of product as yellow solids. $^1$H NMR (200 MHz, CDCl$_3$) δ: 8.12-7.24 (m, 26H), 2.03 (t, 4H), 1.25-0.79 (m, 32H), 0.67 (s, 6H), $^{13}$C NMR (50 MHz, CDCl$_3$) δ: 168.0, 154.4, 151.9, 141.3, 140.5, 136.2, 135.2, 132.6, 131.2, 128.2, 127.2, 126.6, 126.2, 125.4, 121.9, 121.2, 120.3, 55.3, 40.8, 30.3, 29.8, 29.7, 29.5, 24.0, 22.9, 14.3.

Example 13

Synthesis of Fluorophore (7)

7-[2-(4-Benzothiazol-2-yl-phenyl)vinyl]-9,9-didecylfluoren-2-ylamine (0.49 g, 0.7 mmol), K$_2$CO$_3$ (0.78 g, 6.3 mmol), 18-crown-6 (0.56 g, 2.1 mmol), Cu (0.22 g, 3.5 mmol) and iodobenzene (0.29 g, 1.4 mmol) were dissolved in 30 mL of degassed 1,2-dichlorobenzene. 7-[2-(4-Benzothiazol-2-yl-phenyl)vinyl]-9,9-didecylfluoren-2-ylamine was prepared reaction of 7-iodo-2-nitro-9,9-didecylfluorene (prepared as described in Belfield et al. Journal of Organic Chemistry, 2000) with 2-(4-vinylphenyl)-benzothiazole (described in the example above), followed by reduction with graphite and hydrazine hydrate. The reaction mixture was heated at 80° C. for 48 h under nitrogen atmosphere. After confirmation of the disappearance of the starting compound by TLC, the dark brown mixture was cooled to room temperature. The mixture was filtered and evaporated under reduced pressure. Distilled water was poured onto the residue, and the product was extracted with CH$_2$Cl$_2$. The extract was dried over MgSO4, and the solvent was removed under reduced pressure. The residue was chromatographed on a silica gel column using mixed eluent of n-hexane/ethyl acetate (10:1) to give 0.43 g (73% yield) of product as yellow-solids.

Procedures for Making Photosensitive Polymer Compositions

Generally, all solution studies were performed in CH$_2$Cl$_2$. Individual stock solutions containing PAG only (0.5-20 wt %), polymer and PAG (5-50 wt % and 0.5-10 wt %, respectively), PAG and fluorophore (0.5-20 wt % and 0.01-5.0 wt %, respectively), and polymer, PAG, and fluorophore (5-50 wt %, 0.5-20 wt % and 0.01-5 wt %, respectively) were prepared. All polymer solutions (5-50 wt % polymer) were passed through a 0.45 µm glass filter, prior to spin-coating at a spin rate of 1500 rpm for 20 sec. Films were dried under reduced pressure overnight, and their thickness measured by profilometry. Polymer film compositions typically contained 0.01-5.0 wt % of the fluorophore and 0.5-20.0 wt % of PAG, relative to the polymer. The dried films were then exposed to UV light for various durations through a mask and, following mask removal, the two-photon fluorescence imaging was performed on single and multilayered films.

Specifically, individual stock solutions containing PAG only (1.7 wt %), polymer and PAG (18.3 and 1.7 wt %, respectively), PAG and fluorophore (1.7 and 0.16 wt %, respectively), and polymer, PAG, and fluorophore (18.3, 1.7, and 0.16 wt %, respectively) were prepared. From each stock solution, 25 µL was removed and placed into 10 mL volumetric flasks, then filled to volume. Solutions were transferred into a spectrofluorometer quartz cuvette cell fitted with a Teflon stopper and a small magnetic stir bar, which allowed for solution mixing during photoexposure to the broad-band UV light source in the Rayonett photoreactor. All solvents and solutions were deaerated by bubbling with N$_2$ gas prior to spectroscopic measurements, and were carefully protected from exposure to ambient or external light sources. Each solution was exposed for 120 sec, with absorption and fluorescence emission spectra collected at 10 sec intervals.

Polymer solutions (18 wt % polymer) were passed through a 0.45 µm glass filter, prior to spin-coating at a spin rate of 1500 rpm for 20 sec. Films were dried under reduced pressure overnight, and their thickness measured by profilometry. Polymer film compositions contained 0.9 wt % of the fluorophore and 9 wt % of PAG, relative to the polymer. The dried films were then exposed to UV light for various durations through a mask and, following mask removal, the two-photon fluorescence imaging was performed on single and multilayered films.

UTILITY

Fluorene dye 1 was previously shown to undergo two-photon absorption and upconverted fluorescence on exposure to near-IR femtosecond (fs) laser irradiation. The two-photon absorbing dye 1, contains basic nitrogen-containing benzothiazolyl and triarylamino groups that are sensitive to the presence of acids (FIG. 1). Pohers et al. have demonstrated the absorption spectrum of an acid-sensitive dye containing the benzothiazole group red shifts upon photonation in the presence of a PAG (Pohlers et al. Chem. Mater. 1997, 9, 3222). Due to differences in basicity (pK$_b$), fluorene 1 undergoes selective, stepwise protonation, first by protonation of the benzothiazolyl nitrogen then the trarylamino nitrogen. This leads to a mixture of three species as shown in FIG. 1 (1, 2, and 3), each species with distinct UV-visible absorption and fluorescence emission properties. To understand the behavior of the two-photon absorbing fluorophore and predict results expected in solid thin film studies, solution studies were performed in CH$_2$Cl$_2$. Time-dependent UV-visible absorption spectra for a solution containing 1 and the photoacid generator CD1010 (a triarylsulfonium salt) illustrate this nicely, as shown in FIG. 2. Upon irradiation with broadband UV light (300-400 nm, 0.57 mW/cm$^2$), 1 undergoes protonation, resulting in formation of 2 whose absorption spectrum is red shifted by about 100 nm relative to that of 1. The conversion of the neutral fluorophore 1 at early photolysis times (10 sec) results in decreasing absorbance at its maximum at 390 nm, and increasing absorbance at 500 nm upon generation of the protonated form, 2. The red shift was expected since fluorene 1 is of an electron donor-π-acceptor construct and protonation of the benzothiazolyl acceptor increases the electron deficiency of this group, affording a greater dipole moment and polarizability. When 2 undergoes protonation, a new absorption that is blue shifted relative to both 1 and 2 was observed, due to the fact that the once electron-donating diphenylamino group in 1 and 2 has been converted to an electron accepting moiety (quaternary ammonium salt) in 3. The absorption due to the triarylsulfonium salt ($\lambda_{max}$=310 nm) also decreases with time as expected but, for clarity, is not displayed in FIG. 2.

Changes in the fluorescence emission spectra corresponded with the observed changes in the absorption spectra. Protonation of fluorine 1 also resulted in a reduction of its fluorescence emission, while emission at longer wavelengths was observed due to excitation of the longer wavelength absorbing monoprotonated 2 as shown in FIG. 3. As can be seen, the fluorescence emission intensity at ca. 490 nm (390 nm excitation wavelength) decreases with irradiation while, at early photolysis times, emission at ca. 625 nm appears, which then blue shifts upon further protonation to 3. The emission at 625 nm is from monoprotonated 2 upon excitation at 500 nm. Eventually, diprotonation results in a relatively weak, blue shifted emission at ca. 445 nm (from 3). Thus, in addition to observing fluorescence quenching at ca. 490 nm, fluorescence enhancement (creation) at longer wavelengths (ca. 625 nm) is observed upon short photolysis times. As demonstrated in the following section, this behavior facilitates two-channel fluorescence imaging, resulting in contrast due to fluorescence quenching at the shorter wavelengths ($\lambda_{emission}$ of 1 from 425-620 nm) and fluorescence enhancement at longer wavelengths ($\lambda_{emission}$ of 2 from 520-700 nm).

To demonstrate the ability of fluorene 1 to exhibit two-photon upconverted fluorescence emission, fluorescence spectra were recorded upon excitation at a number of wavelengths using fs near-IR excitation. Two-photon upconverted fluorescence spectra ($2.5 \times 10^{-4}$ M, ACN) pumped with fs pulsed, near-IR are illustrated in FIGS. 4a and 4b. The neutral fluorophore 1, displayed upconverted fluorescence emission over a wide pump range, from 680 to 880 nm (FIG. 4a) while, from FIG. 4b, it is readily apparent that maximum two-photon upconverted fluoresence intensity was observed when pumped at 800 nm. To further confirm that fluorine 1 underwent two-photon absorption, the total integrated fluorescence intensity was determined as a function of incident intensity (pump power). Fluorescence from a two-photon absorption process will exhibit a quadratic dependence on incident intensity. Indeed, FIG. 5 confirms that fluorene 1 underwent two-photon absorption as evidenced by the quadratic relationship, between fluorescence emission intensity at several pump powers at two different pump wavelengths.

The structure, time-dependent absorption, and time dependent fluorescence spectra for a PAG upon photolysis are shown in FIGS. 6 and 7.

Next, thin polymer films (ca. 2-3 µm film thickness) were prepared by spin coating (on glass) a mixture of fluorene 1, the photoacid generator, and polystyrene or alternatively, phosphorylated poly(VBC-co-MMA) in a 1:3 v/v solution of acetonitrile/dioxane. Photosensitive polymer film compositions typically contained 0.9 wt. % of fluorene 1 and 9 wt. % of CD1010 relative to the polymer. Films were exposed to UV light through a number of different masks, including TEM grids, Air Force resolution targets, and photolithographic waveguide masks as shown in FIG. 8. After mask removal, two-photon fluorescence image collection was performed on the exposed films in single or multilayers.

Results analogous to those obtained in solution studies were observed but, quite fortuitously, the slower acid generation/protonation rate resulted in formation and stabilization of monoprotonated fluorene 2. With the beam focused in the plane of the fluorophore-containing layer, fluorescence intensity was recorded with both channel 1 (green) and channel 2 (red) simultaneously. The contrast in the "green" channel was due to the decrease in fluorescence of fluorene 1 (whose concentration decreases with irradiation). Contrast in the "red" channel was due to the fluorescence of monoprotonated 2 (whose concentration increases with irradiation).

FIGS. 9, 10, and 11 show photosensitive films exposed using an Air Force image resolution target with images recorded by both channels. The large differences in fluorescence intensity in exposed and unexposed regions can be clearly seen in the graph of FIG. 11c as well as the reverse parity of the images in the two channels. i.e. "positive" and "negative" image formation from one system. Time-dependent studies were performed by irradiating the films for various exposure times to determine the optimal contrast for each detection channel. The fluorescence intensity profiles as a function of exposure time and position across one set of the elements for each image are shown. Optimal exposure time can be established by identifying the intensity profile that would provide the best signal-to-noise ratio, minimizing the hazard of overexposing films that may compromise resolution due to acid diffusion.

For demonstrative purposes, multilayer assemblies were constructed by placing an uncoated glass cover slip between two cover slips coated with patterned photosensitive films, with the coated sides against the middle cover slip as shown in FIG. 12. Three-dimensional two-photon fluorescence imaging was performed on the multilayer structures.

Two-photon fluorescent images of the photosensitive films constructed in a multi-layer configuration (developed via UV exposure through TEM square and hexagonal grid masks) are displayed in FIGS. 13a and 13b. An xy planar scan of each film (hexagonal grid image on the top and square grid image on the bottom) within the multi-layer, by focusing and scanning within the plane of the films, clearly shows the photo-patterned image resulting from formation of the protonated species in exposed areas. A cross-sectional scan, where an xy line scan is stepped in the z dimension (multi-layered image between the grid images in FIG. 13c, clearly displays the separate film layers and demonstrates the three dimensional nature of image formation possible within layered assemblies, and the nondestructive optimal sectioning ability of two-photon fluorescent imaging. The signal readout establishes the possibility for a WORM binary optical data storage medium, where the valleys can be designated as a "0" and the peaks a "1". Based on the findings, photosensitive polymers have been prepared bearing a fluorophore that exhibit high two-photon absorptivity (FIG. 14). The polymer derived from copolymerization with maleic anhydride was modified with a primary amine-containing two-photon absorbing fluorophore, affording the corresponding imide. The UV-visible absorption spectra of the polymer in $CH_2Cl_2$ with PAG (P PAG) and without PAG (P) are shown in FIG. 15. A rapid decrease in absorbance was observed at ca. 400 nm in the mixture containing the fluorophore labeled polymer with PAG upon exposure to a broadband UV light source. The polymer without the PAG in solution also displayed a decreased absorbance at ca. 400 nm, and for clarity, is displayed in the inset graph. The fluorescence spectra of the fluorophore labeled polymer with (P PAG) and without (P) the PAG shown in FIG. 15 revealed two components. One component with the shorter wavelength emission centered at 425 nm, is attributable to the fluorenylimide fluorophore. An additional component produced emission at longer wavelengths (475 nm), and may likely be due to a charge-transfer. Interestingly, fluorescence enhancement at 425 nm was observed in the solution containing only the modified polymer upon excitation at 370 nm. A minimal reduction was observed in the presence of PAG at 400 nm, but a decrease in fluorescence intensity was more apparent at 475 nm, in the range of the second component. Upon excitation at 400 nm, both the polymer with and without the PAG displayed a decrease in fluorescence intensity, with the PAG containing solution demonstrating a more rapid decrease due to protonation of the benzothiazoyl nitrogen by the photogenerated acid.

Photophysical properties indicate the polymer undergoes two-photon upconverted fluorescence, and exhibits the characteristic quadratic behavior to the incident fs near-IR intensity (FIG. 16). Single-photon and two-photon fluorescence spectra for a polyethylene-based photosensitive polymer are shown in FIG. 17.

Next, thin films of the fluorophore labeled polymer with and without the PAG were spin-coated onto glass substrates. Films were exposed to a broadband UV light through TEM grids, an after mask removal, two-photon fluorescence image collection was performed on the exposed films in single or multilayers (800 nm, 115 fs). Interestingly, the polymer films excluding the PAG displayed a fluorescence enhancement in the exposed areas, corresponding to the solution behavior upon excitation at 370 mm. A clear image contrast was obtained, as shown in FIGS. 18-20, reinforced by the high signal-to-noise fluorescence intensity signal observed across the contrast image. The modulation of the fluorescence properties of the photosensitive polymer, in the presence and absence of a photoacid generator, provided image contrast. A multi-layered assembly and bulk two-photon fluorescence lithographic imaging provided both "negative" and "positive" contrast images, demonstrating the possibility of three-dimensional optical data read-out, as illustrated in FIGS. 18, 19, 20, and 21. Three-dimensional, optical sectioning through the film thickness was obtained, where a series of xy planar scans was performed as a function of z position (depth). The fluorescence intensity profile of the polymer film without PAG, through the film thickness was obtained, where the maximum fluorescence intensity was observed at the center of the film.

An opposite contrast image of the polymer containing PAG was observed, relative to the exposed photosensitive polymer without any PAG present. Thus, the modified polymer exhibits an inherent photosensitivity, whereby the fluorescence properties can be modulated without incorporation of a photoacid generator.

Finally, both writing and recording were accomplished by two-photon excitation of a fluorophore/PAG photosensitive polymer film in which writing was accomplished by xy-scans at 740 nm (115 fs, 76 MHz). A schematic diagram of the setup used for this experiment is depicted in FIG. 22. The written image was read by a two-photon fluorescence imaging at 800 nm (115 fs. 76 MHz), as shown in FIG. 23. Thus, image writing and reading has been accomplished via near-IR two-photon excitation of polymer film-containing fluorophore 1 and a photoacid generator. The behavior and relative stability of the photosensitive materials disclosed herein provide for WORM three-dimensional memory systems, with writing and reading accomplished via two-photon excitation and fluorescence imaging, respectively.

The following are advantages of the device of the invention over the previously reported systems.

The photosensitive materials and process for data writing and recording are less complex. The writing is accomplished by excitation of the PAG while readout relies on excitation of the fluorophore. This allows the writing and reading to be decoupled, avoiding photobleaching or photodamage to the fluorophore during the writing procedure, a major improvement. Other advantages include greater sensitivity through fluorescence-based detection, higher stability fluorophores, and multichannel readout that affords greater versatility in data storage and storage density. The increased sensitivity should provide faster data writing and reading rates.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:
1. A photosensitive composition comprising:
(a) a fluorophore compound of Formula IV;

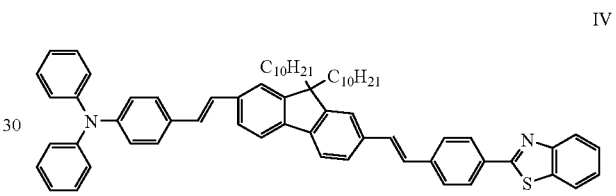

(b) a photoacid generator; and
(c) a polymer binder.
2. A photosensitive composition according to claim 1, wherein the photoacid generator is selected from the group consisting of diphenyl iodonium hexafluorophosphate, diphenyl iodonium hexafluoroarsenate, diphenyl iodonium hexafluoroantimonate, diphenyl p-methoxyphenyl iodonium triflate, diphenyl p-toluenyl iodonium triflate, diphenyl p-isobutylphenyl iodonium triflate, diphenyl p-tert-butylphenyl iodonium triflate, triphenylsulfonium hexafluorophosphate, triphenylsulfonium hexafluoroarsenate, triphenylsulfonium hexafluoroantimonate, triphenylsulfonium triflate, dibutylnaphthylsulfonium triflate and mixtures thereof.

* * * * *